United States Patent
Bolea et al.

(10) Patent No.: US 10,737,094 B2
(45) Date of Patent: Aug. 11, 2020

(54) OBSTRUCTIVE SLEEP APNEA TREATMENT DEVICES, SYSTEMS AND METHODS

(71) Applicant: LivaNova USA, Inc., Houston, TX (US)

(72) Inventors: Stephen L. Bolea, Watertown, MN (US); Thomas B. Hoegh, Edina, MN (US); Brian D. Kuhnley, Maple Grove, MN (US); Dale G. Suilmann, Elk River, MN (US); Bruce J. Persson, Dresser, WI (US); John P. Beck, Savage, MN (US); Sidney F. Hauschild, St. Paul, MN (US); Paula M. Kaplan, St. Paul, MN (US); Adam K. Hoyhtya, Shoreview, MN (US); Wondimeneh Tesfayesus, St. Paul, MN (US); Robert E. Atkinson, White Bear Lake, MN (US)

(73) Assignee: LivaNova USA, Inc., Houston, TX (US)

( * ) Notice: Subject to any disclaimer, the term of this patent is extended or adjusted under 35 U.S.C. 154(b) by 76 days.

(21) Appl. No.: 16/164,551

(22) Filed: Oct. 18, 2018

(65) Prior Publication Data

US 2019/0151656 A1    May 23, 2019

Related U.S. Application Data

(63) Continuation of application No. 12/980,840, filed on Dec. 29, 2010, now Pat. No. 10,105,538, which is a
(Continued)

(51) Int. Cl.
*A61N 1/36* (2006.01)
*A61B 5/053* (2006.01)
(Continued)

(52) U.S. Cl.
CPC .......... *A61N 1/3601* (2013.01); *A61B 5/0538* (2013.01); *A61B 5/4818* (2013.01);
(Continued)

(58) Field of Classification Search
CPC .. A61N 1/3601; A61N 1/0556; A61B 5/0538; A61B 5/4818
See application file for complete search history.

(56) References Cited

U.S. PATENT DOCUMENTS

| 758,030 A | 4/1904 | Carence |
| 1,520,930 A | 12/1924 | Calhoun |

(Continued)

FOREIGN PATENT DOCUMENTS

| EP | 0 900 102 B1 | 7/2004 |
| EP | 0 892 926 B1 | 6/2006 |

(Continued)

OTHER PUBLICATIONS

Campbell et al., "Nasal Continuous positive airway pressure from high flow cannula versus Infant Flow for preterm infants," Journal of Perinatology, Jul. 2006, pp. 546-549, vol. 26 (9), Nature Publishing Group.
(Continued)

*Primary Examiner* — Michael J D Abreu
(74) *Attorney, Agent, or Firm* — Foley & Lardner LLP

(57) ABSTRACT

Devices, systems and methods of neurostimulation for treating obstructive sleep apnea.

20 Claims, 27 Drawing Sheets

Related U.S. Application Data continuation of application No. 12/650,045, filed on Dec. 30, 2009, now Pat. No. 9,744,354.

(60) Provisional application No. 61/204,008, filed on Dec. 31, 2008.

(51) Int. Cl.
*A61B 5/00* (2006.01)
*A61N 1/05* (2006.01)

(52) U.S. Cl.
CPC .......... *A61N 1/0556* (2013.01); *A61N 1/3611* (2013.01); *A61N 1/36139* (2013.01)

(56) References Cited

U.S. PATENT DOCUMENTS

| | | |
|---|---|---|
| 1,701,277 A | 2/1929 | Shindel |
| 1,914,418 A | 6/1933 | Goyena |
| 2,046,664 A | 7/1936 | Weaver |
| 2,151,227 A | 3/1939 | Pawelek |
| 2,237,954 A | 4/1941 | Wilsom |
| 2,243,360 A | 5/1941 | Slatis et al. |
| 2,274,886 A | 3/1942 | Carroll |
| 2,526,586 A | 10/1950 | Shuff |
| 2,693,799 A | 11/1954 | Herman, Jr. |
| 2,777,442 A | 1/1957 | Zelano |
| 2,928,388 A | 3/1960 | Jaroslaw |
| 3,457,917 A | 7/1969 | Mercurio |
| 3,513,839 A | 5/1970 | Vacante |
| 3,680,555 A | 8/1972 | Warncke |
| 3,722,509 A | 3/1973 | Nebel |
| 3,774,618 A | 11/1973 | Avery |
| 3,865,106 A | 2/1975 | Palush |
| 3,884,223 A | 5/1975 | Keindl |
| 3,906,936 A | 9/1975 | Habal |
| 4,160,252 A | 7/1979 | Lucas et al. |
| 4,160,255 A | 7/1979 | Kobayashi |
| 4,178,524 A | 12/1979 | Ritter |
| 4,200,440 A | 4/1980 | Renko |
| 4,220,150 A | 9/1980 | King |
| 4,221,217 A | 9/1980 | Amezcua |
| 4,225,034 A | 9/1980 | Sarovich |
| 4,239,918 A | 12/1980 | Keeley |
| 4,242,987 A | 1/1981 | Viessmann |
| 4,267,831 A | 5/1981 | Aguilar |
| 4,283,867 A | 8/1981 | Brown |
| 4,302,951 A | 12/1981 | Fall et al. |
| 4,313,442 A | 2/1982 | Knudson et al. |
| 4,346,398 A | 8/1982 | Lai |
| 4,374,527 A | 2/1983 | Iversen |
| 4,506,666 A | 3/1985 | Durkan |
| 4,567,892 A | 2/1986 | Plicchi et al. |
| 4,573,481 A | 3/1986 | Bullara |
| 4,777,963 A | 10/1988 | McKenna |
| 4,830,008 A | 5/1989 | Meer |
| 4,899,750 A | 2/1990 | Ekwall |
| 4,915,105 A | 4/1990 | Lee |
| 4,919,136 A | 4/1990 | Alt |
| 4,940,065 A | 7/1990 | Tanagho et al. |
| 4,960,133 A | 10/1990 | Hewson |
| 4,996,983 A | 3/1991 | Amrhein |
| 5,016,808 A | 5/1991 | Heil et al. |
| 5,105,826 A | 4/1992 | Smits et al. |
| 5,121,754 A | 6/1992 | Mullett |
| 5,133,354 A | 7/1992 | Kallok |
| 5,146,918 A | 9/1992 | Kallok et al. |
| 5,158,080 A | 10/1992 | Kallok |
| 5,174,287 A | 12/1992 | Kallok et al. |
| 5,178,156 A | 1/1993 | Takishima et al. |
| 5,190,053 A | 3/1993 | Meer |
| 5,211,173 A | 5/1993 | Kallok et al. |
| 5,215,082 A | 6/1993 | Kallok et al. |
| 5,277,193 A | 1/1994 | Takishima et al. |
| 5,281,219 A | 1/1994 | Kallok |
| 5,300,094 A | 4/1994 | Kallok et al. |
| 5,324,321 A | 6/1994 | Pohndorf et al. |
| 5,335,657 A | 8/1994 | Terry, Jr. et al. |
| 5,344,438 A | 9/1994 | Testerman et al. |
| 5,388,578 A | 2/1995 | Yomtov et al. |
| 5,392,773 A | 2/1995 | Bertrand |
| 5,417,205 A | 5/1995 | Wang |
| 5,425,359 A | 6/1995 | Liou |
| 5,458,629 A | 10/1995 | Baudino et al. |
| 5,483,969 A | 1/1996 | Testerman et al. |
| 5,485,836 A | 1/1996 | Lincoln |
| 5,485,851 A | 1/1996 | Erickson |
| 5,511,543 A | 4/1996 | Shirley |
| 5,522,382 A | 6/1996 | Sullivan et al. |
| 5,522,862 A | 6/1996 | Testerman et al. |
| 5,531,778 A | 7/1996 | Maschino et al. |
| 5,540,732 A | 7/1996 | Testerman |
| 5,540,733 A | 7/1996 | Testerman et al. |
| 5,540,734 A | 7/1996 | Zabara |
| 5,546,938 A | 8/1996 | McKenzie |
| 5,549,655 A | 8/1996 | Erickson |
| 5,568,808 A | 10/1996 | Rimkus |
| 5,591,216 A | 1/1997 | Testerman et al. |
| 5,630,411 A | 5/1997 | Holscher |
| 5,682,881 A | 11/1997 | Winthrop et al. |
| 5,697,105 A | 12/1997 | White |
| 5,697,363 A | 12/1997 | Hart |
| 5,730,122 A | 3/1998 | Lurie |
| 5,740,798 A | 4/1998 | McKinney |
| 5,752,511 A | 5/1998 | Simmons et al. |
| 5,787,884 A | 8/1998 | Tovey |
| 5,848,589 A | 12/1998 | Welnetz |
| 5,855,552 A | 1/1999 | Houser et al. |
| 5,890,491 A | 4/1999 | Rimkus |
| 5,895,360 A | 4/1999 | Christopherson et al. |
| 5,922,014 A | 7/1999 | Warman et al. |
| 5,938,596 A | 8/1999 | Woloszko et al. |
| 5,944,680 A | 8/1999 | Christopherson et al. |
| 5,947,119 A | 9/1999 | Reznick |
| 6,010,459 A | 1/2000 | Silkoff et al. |
| 6,015,389 A | 1/2000 | Brown |
| 6,021,352 A | 2/2000 | Christopherson et al. |
| 6,021,354 A | 2/2000 | Warman et al. |
| 6,029,667 A | 2/2000 | Lurie |
| 6,041,780 A | 3/2000 | Richard et al. |
| 6,051,052 A | 4/2000 | Monereau et al. |
| 6,066,165 A | 5/2000 | Racz |
| 6,098,624 A | 8/2000 | Utamaru |
| 6,109,262 A | 8/2000 | Tovey |
| 6,119,690 A | 9/2000 | Pantaleo |
| 6,126,611 A | 10/2000 | Bourgeois et al. |
| 6,132,384 A | 10/2000 | Christopherson et al. |
| 6,198,970 B1 | 3/2001 | Freed et al. |
| 6,201,994 B1 | 3/2001 | Warman et al. |
| 6,217,527 B1 | 4/2001 | Selmon et al. |
| 6,221,049 B1 | 4/2001 | Selmon et al. |
| 6,231,546 B1 | 5/2001 | Milo et al. |
| 6,240,316 B1 | 5/2001 | Richmond et al. |
| 6,244,267 B1 | 6/2001 | Eifrig |
| 6,251,126 B1 | 6/2001 | Ottenhoff et al. |
| 6,269,269 B1 | 7/2001 | Ottenhoff et al. |
| 6,345,202 B2 | 2/2002 | Richmond et al. |
| 6,366,815 B1 | 4/2002 | Haugland et al. |
| 6,460,539 B1 | 10/2002 | Japuntich et al. |
| 6,484,725 B1 | 11/2002 | Chi |
| 6,511,458 B2 | 1/2003 | Milo et al. |
| 6,514,217 B1 | 2/2003 | Selmon et al. |
| 6,542,776 B1 | 4/2003 | Gordon et al. |
| 6,561,188 B1 | 5/2003 | Ellis |
| 6,587,725 B1 | 7/2003 | Durand et al. |
| 6,600,956 B2 | 7/2003 | Maschino et al. |
| 6,606,521 B2 | 8/2003 | Paspa et al. |
| 6,626,179 B1 | 9/2003 | Pedley |
| 6,636,767 B1 | 10/2003 | Knudson et al. |
| 6,641,542 B2 | 11/2003 | Cho et al. |
| 6,647,289 B2 | 11/2003 | Prutchi |
| 6,651,652 B1 | 11/2003 | Ward |
| 6,718,982 B2 | 4/2004 | Smith et al. |
| 6,719,725 B2 | 4/2004 | Milo et al. |

(56) References Cited

U.S. PATENT DOCUMENTS

| | | |
|---|---|---|
| 6,721,603 B2 | 4/2004 | Zabara et al. |
| 6,772,015 B2 | 8/2004 | Dahl et al. |
| 6,776,162 B2 | 8/2004 | Wood |
| 6,799,575 B1 | 10/2004 | Carter |
| 6,819,958 B2 | 11/2004 | Weiner et al. |
| 6,829,503 B2 | 12/2004 | Alt |
| 6,829,508 B2 | 12/2004 | Schulman et al. |
| RE38,705 E | 2/2005 | Hill et al. |
| 6,876,885 B2 | 4/2005 | Swoyer et al. |
| 6,881,192 B1 | 4/2005 | Park |
| 6,883,518 B2 | 4/2005 | Mittelstadt et al. |
| 6,890,306 B2 | 5/2005 | Poezevera |
| 6,907,295 B2 | 6/2005 | Gross et al. |
| 6,904,320 B2 | 7/2005 | Park et al. |
| 6,928,324 B2 | 8/2005 | Park et al. |
| 6,978,171 B2 | 12/2005 | Goetz et al. |
| 6,997,177 B2 | 2/2006 | Wood |
| 7,027,869 B2 | 4/2006 | Danek et al. |
| 7,054,692 B1 | 5/2006 | Whitehurst et al. |
| 7,065,410 B2 | 6/2006 | Bardy et al. |
| 7,082,331 B1 | 7/2006 | Park et al. |
| 7,087,053 B2 | 8/2006 | Vanney |
| 7,089,932 B2 | 8/2006 | Dodds |
| 7,094,206 B2 | 8/2006 | Hoffman |
| 7,117,036 B2 | 10/2006 | Florio |
| 7,128,717 B1 | 10/2006 | Thach et al. |
| 7,142,919 B2 | 11/2006 | Hine et al. |
| 7,149,573 B2 | 12/2006 | Wang |
| 7,152,604 B2 | 12/2006 | Hickle et al. |
| 7,155,278 B2 | 12/2006 | King et al. |
| 7,156,098 B2 | 1/2007 | Dolezal et al. |
| 7,160,252 B2 | 1/2007 | Cho et al. |
| 7,160,255 B2 | 1/2007 | Saadat |
| 7,178,524 B2 | 2/2007 | Noble |
| 7,200,440 B2 | 4/2007 | Kim et al. |
| 7,225,034 B2 | 5/2007 | Ries et al. |
| 7,239,320 B1 | 7/2007 | Hall et al. |
| 7,239,918 B2 | 7/2007 | Strother et al. |
| 7,242,987 B2 | 7/2007 | Holleman et al. |
| 7,283,867 B2 | 10/2007 | Strother et al. |
| 7,302,951 B2 | 12/2007 | Mittelstadt et al. |
| 7,313,442 B2 | 12/2007 | Velasco et al. |
| 7,346,398 B2 | 3/2008 | Gross et al. |
| 7,366,572 B2 | 4/2008 | Heruth et al. |
| 7,396,333 B2 | 7/2008 | Stahmann et al. |
| 7,438,686 B2 | 10/2008 | Cho et al. |
| 7,453,928 B2 | 11/2008 | Ten et al. |
| 7,463,928 B2 | 12/2008 | Lee et al. |
| 7,473,227 B2 | 1/2009 | Hsu et al. |
| 7,515,968 B2 | 4/2009 | Metzler et al. |
| 7,524,292 B2 | 4/2009 | Cho et al. |
| 7,561,922 B2 | 7/2009 | Cohen et al. |
| 7,591,265 B2 | 9/2009 | Lee et al. |
| 7,596,413 B2 | 9/2009 | Libbus et al. |
| 7,596,414 B2 | 9/2009 | Whitehurst et al. |
| 7,627,375 B2 | 12/2009 | Bardy et al. |
| 7,630,771 B2 | 12/2009 | Cauller |
| 7,634,315 B2 | 12/2009 | Cholette |
| 7,636,602 B2 | 12/2009 | Baru Fassio et al. |
| 7,657,311 B2 | 2/2010 | Bardy et al. |
| 7,660,632 B2 | 2/2010 | Kirby et al. |
| 7,662,105 B2 | 2/2010 | Hatlestad |
| 7,672,728 B2 | 3/2010 | Libbus et al. |
| 7,672,729 B2 | 3/2010 | Koh et al. |
| 7,680,537 B2 | 3/2010 | Stahmann et al. |
| 7,680,538 B2 | 3/2010 | Durand et al. |
| 7,684,869 B2 | 3/2010 | Bradley et al. |
| 7,697,984 B2 | 4/2010 | Hill et al. |
| 7,697,990 B2 | 4/2010 | Ujhazy et al. |
| 7,717,848 B2 | 5/2010 | Heruth et al. |
| 7,720,534 B2 | 5/2010 | Bardy et al. |
| 7,725,195 B2 | 5/2010 | Lima et al. |
| 7,725,198 B2 | 5/2010 | Cross et al. |
| 7,734,340 B2 | 6/2010 | De Ridder |
| 7,734,348 B2 | 6/2010 | Zhang et al. |
| 7,738,952 B2 | 6/2010 | Yun et al. |
| 7,747,323 B2 | 6/2010 | Libbus et al. |
| 7,751,880 B1 | 7/2010 | Cholette |
| 7,751,885 B2 | 7/2010 | Bardy et al. |
| 7,758,384 B2 | 7/2010 | Alexander et al. |
| 7,765,000 B2 | 7/2010 | Zhang et al. |
| 7,769,461 B2 | 8/2010 | Whitehurst et al. |
| 7,783,353 B2 | 8/2010 | Libbus et al. |
| 7,785,262 B2 | 8/2010 | Melker et al. |
| 7,787,959 B1 | 8/2010 | Morgan |
| 7,792,590 B1 | 9/2010 | Pianca et al. |
| 7,797,050 B2 | 9/2010 | Libbus et al. |
| 7,797,057 B2 | 9/2010 | Harris |
| 7,797,058 B2 | 9/2010 | Mrva et al. |
| 7,805,195 B2 | 9/2010 | Zealear |
| 7,809,442 B2 | 10/2010 | Bolea et al. |
| 7,813,797 B2 | 10/2010 | Bardy et al. |
| 7,813,802 B2 | 10/2010 | Tcheng et al. |
| 7,813,809 B2 | 10/2010 | Strother et al. |
| 7,818,063 B2 | 10/2010 | Wallace et al. |
| 7,822,486 B2 | 10/2010 | Foster et al. |
| 8,221,049 B1 | 7/2012 | Westendorf et al. |
| 2001/0010010 A1 | 7/2001 | Richmond et al. |
| 2001/0031929 A1 | 10/2001 | O'Toole |
| 2002/0010495 A1 | 1/2002 | Freed et al. |
| 2002/0049479 A1 | 4/2002 | Pitts |
| 2002/0092527 A1 | 7/2002 | Wood |
| 2002/0128700 A1 | 9/2002 | Cross, Jr. |
| 2002/0165462 A1 | 11/2002 | Westbrook et al. |
| 2002/0166556 A1 | 11/2002 | Jacob |
| 2002/0195108 A1 | 12/2002 | Mittelstadt et al. |
| 2002/0195109 A1 | 12/2002 | Mittelstadt et al. |
| 2003/0034031 A1 | 2/2003 | Lev et al. |
| 2003/0078643 A1 | 4/2003 | Schulman et al. |
| 2003/0083696 A1 | 5/2003 | Avital |
| 2003/0093128 A1 | 5/2003 | Freed et al. |
| 2003/0106555 A1 | 6/2003 | Tovey |
| 2003/0106556 A1 | 6/2003 | Alperovich et al. |
| 2003/0114895 A1 | 6/2003 | Gordon et al. |
| 2003/0114905 A1 | 6/2003 | Kuzma |
| 2003/0167018 A1 | 9/2003 | Wyckoff |
| 2003/0195571 A1 | 10/2003 | Burnes et al. |
| 2003/0209145 A1 | 11/2003 | Soper |
| 2003/0216789 A1 | 11/2003 | Deem et al. |
| 2004/0015204 A1 | 1/2004 | Whitehurst et al. |
| 2004/0020489 A1 | 2/2004 | Gillespie et al. |
| 2004/0049241 A1 | 3/2004 | Campos |
| 2004/0055603 A1 | 3/2004 | Bruce |
| 2004/0073272 A1 | 4/2004 | Knudson et al. |
| 2004/0089303 A1 | 5/2004 | Chien |
| 2004/0111139 A1 | 6/2004 | McCreery |
| 2004/0116819 A1 | 6/2004 | Alt |
| 2004/0138581 A1 | 7/2004 | Frei et al. |
| 2004/0162499 A1 | 8/2004 | Nagai et al. |
| 2004/0194784 A1 | 10/2004 | Bertrand |
| 2004/0215288 A1 | 10/2004 | Lee et al. |
| 2004/0230278 A1 | 11/2004 | Dahl et al. |
| 2004/0233058 A1 | 11/2004 | Dodds |
| 2004/0260310 A1 | 12/2004 | Harris |
| 2004/0261791 A1 | 12/2004 | Horian |
| 2005/0004610 A1 | 1/2005 | Kim et al. |
| 2005/0010265 A1 | 1/2005 | Baru Fassio et al. |
| 2005/0038490 A1 | 2/2005 | Gross et al. |
| 2005/0039757 A1 | 2/2005 | Wood |
| 2005/0043644 A1 | 2/2005 | Stahmann et al. |
| 2005/0043772 A1 | 2/2005 | Stahmann et al. |
| 2005/0076908 A1 | 4/2005 | Lee et al. |
| 2005/0085865 A1 | 4/2005 | Tehrani |
| 2005/0085866 A1 | 4/2005 | Tehrani |
| 2005/0085868 A1 | 4/2005 | Tehrani et al. |
| 2005/0085869 A1 | 4/2005 | Tehrani et al. |
| 2005/0085874 A1 | 4/2005 | Davis et al. |
| 2005/0098176 A1 | 5/2005 | Hoffrichter |
| 2005/0101833 A1 | 5/2005 | Hsu et al. |
| 2005/0119711 A1 | 6/2005 | Cho et al. |
| 2005/0139216 A1 | 6/2005 | Mittelstadt et al. |
| 2005/0165457 A1 | 7/2005 | Benser et al. |
| 2005/0209513 A1 | 9/2005 | Heruth et al. |
| 2005/0209643 A1 | 9/2005 | Heruth et al. |

(56) References Cited

U.S. PATENT DOCUMENTS

| | | |
|---|---|---|
| 2005/0234523 A1 | 10/2005 | Levin et al. |
| 2005/0235992 A1 | 10/2005 | Djupesland |
| 2005/0240241 A1 | 10/2005 | Yun et al. |
| 2005/0251216 A1 | 11/2005 | Hill et al. |
| 2005/0261747 A1 | 11/2005 | Schuler et al. |
| 2005/0267380 A1 | 12/2005 | Poezevara |
| 2005/0267547 A1 | 12/2005 | Knudson et al. |
| 2005/0277844 A1 | 12/2005 | Stroether et al. |
| 2005/0277999 A1 | 12/2005 | Strother et al. |
| 2005/0278000 A1 | 12/2005 | Strother et al. |
| 2006/0005842 A1 | 1/2006 | Rashad et al. |
| 2006/0025828 A1 | 2/2006 | Armstrong et al. |
| 2006/0030919 A1 | 2/2006 | Mrva et al. |
| 2006/0032497 A1 | 2/2006 | Doshi |
| 2006/0052836 A1 | 3/2006 | Kim et al. |
| 2006/0058588 A1 | 3/2006 | Zdeblick |
| 2006/0058852 A1 | 3/2006 | Koh et al. |
| 2006/0064029 A1 | 3/2006 | Arad (Abboud) |
| 2006/0064138 A1 | 3/2006 | Velasco et al. |
| 2006/0079802 A1 | 4/2006 | Jensen et al. |
| 2006/0095088 A1 | 5/2006 | De Ridder |
| 2006/0111755 A1 | 5/2006 | Stone et al. |
| 2006/0116739 A1 | 6/2006 | Betser et al. |
| 2006/0129189 A1 | 6/2006 | George et al. |
| 2006/0135886 A1 | 6/2006 | Lippert et al. |
| 2006/0136024 A1 | 6/2006 | Cohen et al. |
| 2006/0142815 A1 | 6/2006 | Tehrani et al. |
| 2006/0144398 A1 | 7/2006 | Doshi et al. |
| 2006/0149345 A1 | 7/2006 | Boggs et al. |
| 2006/0150978 A1 | 7/2006 | Doshi et al. |
| 2006/0150979 A1 | 7/2006 | Doshi et al. |
| 2006/0150980 A1 | 7/2006 | Kim |
| 2006/0167497 A1 | 7/2006 | Armstrong et al. |
| 2006/0184204 A1 | 8/2006 | He |
| 2006/0195170 A1 | 8/2006 | Cohen et al. |
| 2006/0211951 A1 | 9/2006 | Milijasevic et al. |
| 2006/0224209 A1 | 10/2006 | Meyer |
| 2006/0224211 A1 | 10/2006 | Durand et al. |
| 2006/0241506 A1 | 10/2006 | Melker et al. |
| 2006/0241708 A1 | 10/2006 | Boute |
| 2006/0247729 A1 | 11/2006 | Tehrani et al. |
| 2006/0259079 A1 | 11/2006 | King |
| 2006/0264777 A1 | 11/2006 | Drew |
| 2006/0266369 A1 | 11/2006 | Atkinson et al. |
| 2006/0271118 A1 | 11/2006 | Libbus et al. |
| 2006/0271137 A1 | 11/2006 | Stanton-Hicks |
| 2006/0282127 A1 | 12/2006 | Zealear |
| 2006/0293720 A1 | 12/2006 | Dilorenzo |
| 2006/0293723 A1 | 12/2006 | Whitehurst et al. |
| 2007/0021785 A1 | 1/2007 | Inman et al. |
| 2007/0027482 A1 | 2/2007 | Parnis et al. |
| 2007/0038265 A1 | 2/2007 | Tcheng et al. |
| 2007/0043411 A1 | 2/2007 | Foster et al. |
| 2007/0095347 A1 | 5/2007 | Lampotang et al. |
| 2007/0125379 A1 | 7/2007 | Pierro et al. |
| 2007/0175478 A1 | 8/2007 | Brunst |
| 2007/0227542 A1 | 10/2007 | Kashmakov et al. |
| 2007/0277832 A1 | 12/2007 | Doshi et al. |
| 2007/0283692 A1 | 12/2007 | Tetsuka et al. |
| 2007/0283962 A1 | 12/2007 | Doshi et al. |
| 2007/0295338 A1 | 12/2007 | Loomas et al. |
| 2008/0023007 A1 | 1/2008 | Dolezal et al. |
| 2008/0027480 A1 | 1/2008 | Van Der Burg et al. |
| 2008/0041373 A1 | 2/2008 | Doshi et al. |
| 2008/0163875 A1 | 7/2008 | Aarestad et al. |
| 2008/0183254 A1 | 7/2008 | Bly et al. |
| 2008/0188947 A1 | 8/2008 | Sanders |
| 2009/0270707 A1 | 10/2009 | Alfoqaha et al. |
| 2009/0276024 A1 | 11/2009 | Bonde et al. |
| 2009/0308395 A1 | 12/2009 | Lee et al. |
| 2009/0318986 A1 | 12/2009 | Alo et al. |
| 2009/0326408 A1 | 12/2009 | Moon |
| 2010/0016749 A1 | 1/2010 | Atsma et al. |
| 2010/0036285 A1 | 2/2010 | Govari et al. |
| 2010/0047376 A1 | 2/2010 | Imbeau et al. |
| 2010/0076536 A1 | 3/2010 | Merz et al. |
| 2010/0094379 A1 | 4/2010 | Meadows et al. |
| 2010/0100150 A1 | 4/2010 | Kirby et al. |
| 2010/0125310 A1 | 5/2010 | Wilson et al. |
| 2010/0131029 A1 | 5/2010 | Durand et al. |
| 2010/0137931 A1 | 6/2010 | Hopper et al. |
| 2010/0137949 A1 | 6/2010 | Mazgalev et al. |
| 2010/0137956 A1 | 6/2010 | Osypka |
| 2010/0152553 A1 | 6/2010 | Ujhazy et al. |
| 2010/0174341 A1 | 7/2010 | Bolea et al. |
| 2010/0228133 A1 | 9/2010 | Averina et al. |
| 2010/0228317 A1 | 9/2010 | Libbus et al. |
| 2010/0241207 A1 | 9/2010 | Bluger |
| 2010/0257729 A1 | 10/2010 | Alexander et al. |
| 2010/0262209 A1 | 10/2010 | King et al. |

FOREIGN PATENT DOCUMENTS

| | | |
|---|---|---|
| EP | 1 854 494 A1 | 11/2007 |
| JP | 53-118893 A | 10/1978 |
| JP | 09-294819 A | 11/1997 |
| JP | 2000-508601 A | 5/2000 |
| JP | 2000-508562 A | 7/2000 |
| JP | 2003-305135 A | 10/2003 |
| JP | 2004-508908 A | 3/2004 |
| JP | 2004-532707 A | 10/2004 |
| JP | 3688301 B2 | 6/2005 |
| JP | 2005-521485 A | 7/2005 |
| JP | 2007-021156 A | 2/2007 |
| WO | WO-98/20938 A1 | 5/1998 |
| WO | WO-02/24279 A1 | 3/2002 |
| WO | WO-03/000133 A1 | 1/2003 |
| WO | WO-03/000347 A1 | 1/2003 |
| WO | WO-03/082393 A1 | 10/2003 |
| WO | WO-2005/004993 A1 | 1/2005 |
| WO | WO-2006/045251 A1 | 5/2006 |
| WO | WO-2006/063339 A2 | 6/2006 |
| WO | WO-2007/134458 A1 | 11/2007 |

OTHER PUBLICATIONS

De Almeida et al., "Nasal pressure recordings to detect obstructive sleep apnea," Sleep and Breathing, Feb. 25, 2006, pp. 62-69, vol. 10 (2), Springer Heidelberg.

Goding Jr et al., "Relief of Upper Airway Obstruction With Hypoglossal Nerve Stimulation in the Canine", The Laryngoscope, Feb. 1998, pp. 162-169, vol. 108, Lippincott-Raven Publishers, U.S.A.

Kirkness et al., "Nasal airflow dynamics: mechanisms and responses associated with an external nasal dilator strip," University of Western Sydney, T.C. Amis School of Science, Department of Respiratory Medicine, Westmead Hospital and University of Sydney, Westmead, Australia, 2000.

Mahadevia et al., "Effects of expiratory positive airway pressure on sleep-induced respiratory abnormalities in patients with hypersomnia-sleep apnea syndrome," Am. Rev. Respir. Cis., Feb. 1983, vol. 128, pp. 708-711.

Noseda et al., "Compliance with nasal continuous positive airway pressure assessed with a pressure monitor: pattern of use and influence of sleep habits," Chest Clinics and Sleep Laboratories, Hôpitaux Erasmé et Brugmann, Université Libre de Bruxelles, Brussels, Belgium, 2000, vol. 94, pp. 76-81.

Paquereau et al., "Positive pressure titration in the treatment of obstructive sleep apnea syndrome using continuous airway positive pressure," Revue Des Maladies Respiratoires, Apr. 2000, pp. 459-465, vol. 17 (2), Masson Editeur.

Sahin et al., "Chronic recording of hypoglossal nerve activity in a dog model of upper airway obstruction", Journal of Applied Physiology 87 (6), 1999, The American Physiological Society, pp. 2197-2206.

Saslow et al., "Work of breathing using high-flow nasal cannula in preterm infants," Journal of Perinatology, May 11, 2006, pp. 476-480, vol. 26 (8), Nature Publishing Group.

Spence et al., "High-flow nasal cannula as a device to provide continuous positive airway pressure in infants," Journal of Perinatology, Dec. 2007, pp. 772-775, vol. 27 (12), Nature Publishing Group.

(56) References Cited

OTHER PUBLICATIONS

Tiran et al., "An Improved Device for Posterior Rhinomanometry to Measure Nasal Resistance," Journal of Biomechnical Engineering, Nov. 2005, vol. 127, pp. 994-997.

Trevisanuto et al., "A new device for administration of continuous positive airway pressure in preterm infants: comparison with a standard nasal CPAP continuous positive airway pressure system," Intensive Care Medicine, Apr. 2005, pp. 859-864, vol. 31 (6), Springer-Verlag.

Verse et al., "New developments in the therapy of obstructive sleep apnea," European Archives of Oto-Rhino-Laryngology, Jan. 2001, pp. 31-37, vol. 258 (1), Springer-Verlag.

| Symbol | Description |
|---|---|
| P | MASK PRESSURE |
| P=HOLD | PRESSURE IS SET TO ELIMINATE FLOW RESTRICTION |
| ↓P1 | DECREASE MASK PRESSURE 1 cmH2O |
| S(A) | STIMULATION INTENSITY SET TO A mA |
| S(B) | STIMULATION INTENSITY SET TO B mA |
| dS | SMALLEST AVAILABLE INCREMENT OF STIMULATION INTENSITY. EITHER 0.1 mA OR 0.25 mA. |
| S(B)=S(A)+dS | STIM INTENSITY FOR "B" SET TO "A" PLUS SMALLEST AVAILABLE INCREMENT |
| ΔS | STIM INTENSITY CONTRAST. LARGEST ALLOWED DIFFERENCE BETWEEN A AND B STIMULATION INTENSITIES. |
| S(B)=S(A)+ΔS? | IS STIM INTENSITY "B" EQUAL TO "a" PLUS LARGEST ALLOWED STIM INTENSITY CONTRAST. |
| ↑S(A) | INCREMENT CHANNEL A STIM INTENSITY BY SMALLEST AVAILABLE INCREMENT. |
| ↑S(B) | INCREMENT CHANNEL B STIM INTENSITY BY SMALLEST AVAILABLE INCREMENT. |
| F(0) | FLOW DURING NON-STIMULATED BREATH. |
| F(A) | FLOW DURING S(A) |
| F(B) | FLOW DURING S(B) |
| F(0) = RESTRICTED? | IS FLOW RESTRICTED DURING NON-STIMULATED BREATH? |
| F(A) = RESTRICTED? | IS FLOW RESTRICTED DURING S(A)? |
| F(A)>F(0)? | IS FLOW DURING S(A) GREATER THAN FLOW DURING NON-STIMULATED BREATH? |
| F(B)>F(A)? | IS FLOW DURING S(B) GREATER THAN FLOW DURING S(A)? |
| S=OFF | STIMULATION TURNED OFF. |
| S=0A | S(A) IS DELIVERED ON EVERY OTHER BREATH. |
| S=0A0B | OUT OF A 4 BREATH SERIES, THE 1ST AND 3RD BREATHS ARE NOT STIMMED, THE S(A) IS DELIVERED ON THE 2ND BREATH AND S(B) IS DELIVERED ON THE 4TH BREATH |

FIG. 18B

OBSTRUCTIVE SLEEP APNEA TREATMENT DEVICES, SYSTEMS AND METHODS

CROSS-REFERENCE TO RELATED APPLICATIONS

This patent application is a continuation of U.S. patent application Ser. No. 12/980,840, filed Dec. 29, 2010, which is a continuation of U.S. patent application Ser. No. 12/650, 045, filed Dec. 30, 2009, which claims the benefits of priority to U.S. Provisional Patent Application No. 61/204, 008, filed on Dec. 31, 2008. This patent application is also related to U.S. patent application Ser. Nos. 11/907,532 and 11/907,533, both filed on Oct. 12, 2007, corresponding to U.S. Patent Application Publication Nos. 2008/0103407 and 2008/0103545, respectively. The entire contents of each of these applications is incorporated herein by reference.

FIELD OF THE INVENTION

The inventions described herein relate to devices, systems and associated methods for treating sleep disordered breathing. More particularly, the inventions described herein relate to devices, systems and methods for treating obstructive sleep apnea.

BACKGROUND OF THE INVENTION

Obstructive sleep apnea (OSA) is highly prevalent, affecting one in five adults in the United States. One in fifteen adults has moderate to severe OSA requiring treatment. Untreated OSA results in reduced quality of life measures and increased risk of disease including hypertension, stroke, heart disease, etc.

Continuous positive airway pressure (CPAP) is a standard treatment for OSA. While CPAP is non-invasive and highly effective, it is not well tolerated by patients. Patient compliance for CPAP is often reported to be between 40% and 60%.

Surgical treatment options for OSA are available too. However, they tend to be highly invasive (result in structural changes), irreversible, and have poor and/or inconsistent efficacy. Even the more effective surgical procedures are undesirable because they usually require multiple invasive and irreversible operations, they may alter a patient's appearance (e.g., maxillo-mandibular advancement), and/or they may be socially stigmatic (e.g., tracheostomy).

U.S. Pat. No. 4,830,008 to Meer proposes hypoglossal nerve stimulation as an alternative treatment for OSA. An example of an implanted hypoglossal nerve stimulator for OSA treatment is the Inspire™ technology developed by Medtronic, Inc. (Fridely, Minn.). The Inspire device is not FDA approved and is not for commercial sale. The Inspire device includes an implanted neurostimulator, an implanted nerve cuff electrode connected to the neurostimulator by a lead, and an implanted intra-thoracic pressure sensor for respiratory feedback and stimulus trigger. The Inspire device was shown to be efficacious (approximately 75% response rate as defined by a 50% or more reduction in RDI and a post RDI of ≤20) in an eight patient human clinical study, the results of which were published by Schwartz et al. and Eisele et al. However, both authors reported that only three of eight patients remained free from device malfunction, thus demonstrating the need for improvements.

SUMMARY OF THE INVENTION

To address this and other unmet needs, the present invention provides, in exemplary non-limiting embodiments, devices, systems and methods for nerve stimulation for OSA therapy as described in the following detailed description.

BRIEF DESCRIPTION OF THE DRAWINGS

It is to be understood that both the foregoing summary and the following detailed description are exemplary. Together with the following detailed description, the drawings illustrate exemplary embodiments and serve to explain certain principles. In the drawings:

FIGS. 15A, 15B, 15C, 16A, 16B, 17, 18A and 18B are charts illustrating various therapy titration methodologies.

DETAILED DESCRIPTION OF EXEMPLARY EMBODIMENTS

The following detailed description should be read with reference to the drawings in which similar elements in different drawings are numbered the same. The drawings, which are not necessarily to scale, depict illustrative embodiments and are not intended to limit the scope of the invention.

Overall System

Figure 1:
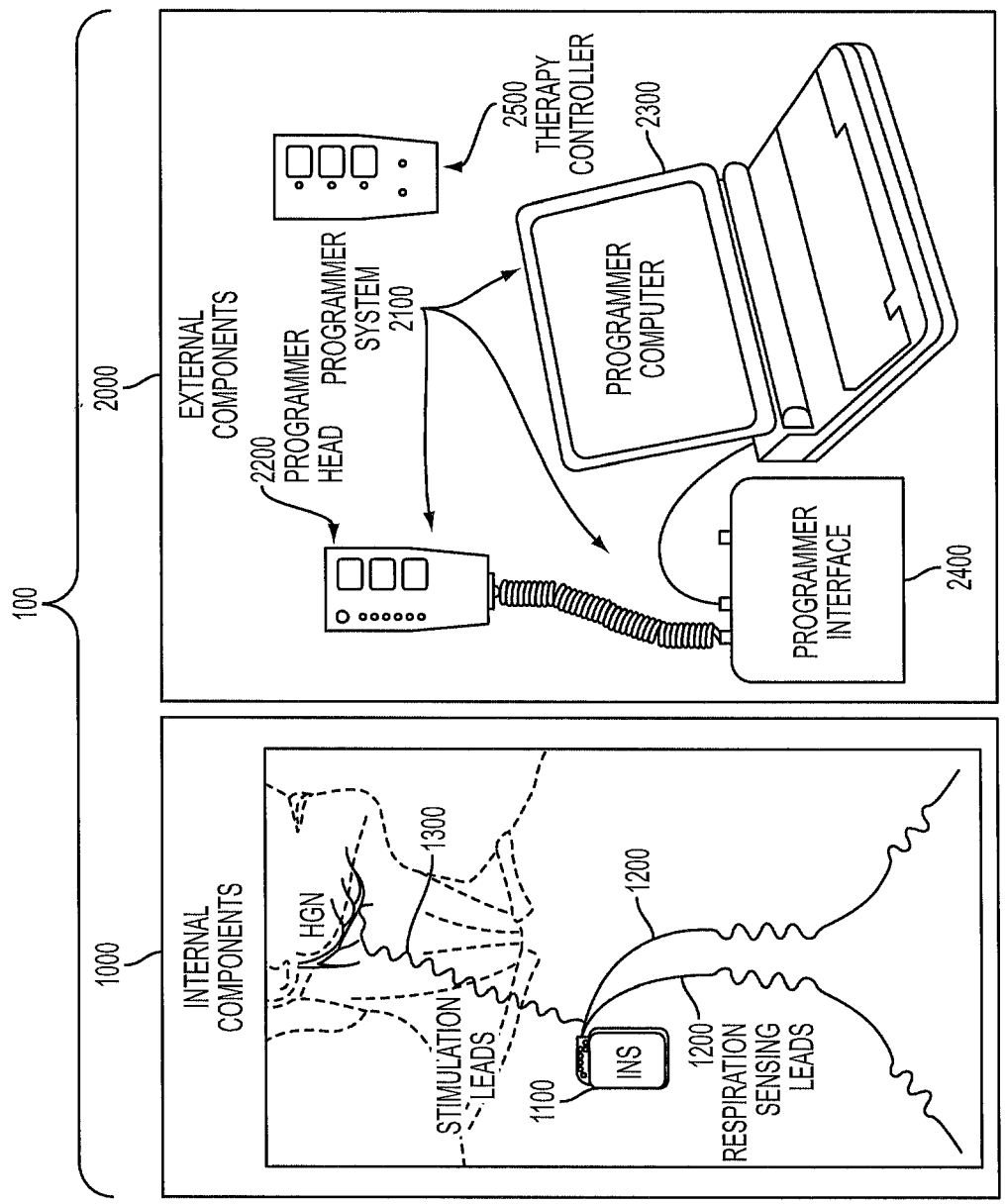
FIG. 1 is a schematic illustration of a system according to an embodiment of the present invention, including internal (chronically implanted) and external components.

FIG. 1 schematically illustrates a hypoglossal nerve stimulation (HGNS) system 100 comprising internal components 1000 and external components 2000. The HGNS system 100 treats obstructive sleep apnea (OSA) by restoring neuromuscular activity to the genioglossus muscle via stimulation of the hypoglossal nerve (HGN) synchronous with inspiration to mitigate upper airway collapse during sleep. Stimulation is generated by an implantable neurostimulator (INS) 1100, synchronized with inspiration as measured by respiration sensing leads (RSLs) 1200 using bio-impedance, and delivered to the hypoglossal nerve by a stimulation lead (STL) 1300. A programmer system 2100 and a therapy controller 2500 are wirelessly linked to the INS 1100. The programmer system 2100 includes a computer 2300, a programmer interface 2400, and a programmer head 2200. The programmer system 2100 is used by the physician to control and program the INS 1100 during surgery and therapy titration, and the therapy controller 2500 is used by the patient to control limited aspects of therapy delivery.

The implanted components 1000 of the HGNS system 100 include the INS 1100, STL 1300, and RSLs 1200. The INS is designed to accommodate one or two STLs 1300 and one or two RSLs 1200. One STL 1300 may be used for unilateral implantation and unilateral hypoglossal nerve stimulation. Two STLs 1300 may be used for bilateral implantation on both the right and left hypoglossal nerves to enhance the effects of stimulation. Alternatively, a second STL 1300 may be used as a back-up in the event of re-operation necessitated by failure or suboptimal placement of the first STL 1300. Similarly, one RSL 1200 may be used for respiration detection, but two RSLs 1200 may be used for enhanced sensing capability or redundancy. Alternatively, a second RSL 1200 may be used as a back-up in the event of re-operation necessitated by failure or suboptimal placement of the first RSL 1200. Port plugs (not shown) may be used to seal the unused ports in the header of the INS 1100. If only one STL 1300 and one RSL 1200 are to be used, the INS 1100 may be simplified to accommodate one of each lead, thus reducing the size and complexity of the INS 1100, as well as increasing battery longevity. For purposes of illustration, not limitation, the INS 1100 is shown with two RSLs 1200 and one STL 1300.

The implanted components 1000 may be surgically implanted with the patient under general anesthesia. The INS 1100 may be implanted in a subcutaneous pocket inferior to the clavicle over the pectoralis fascia. The distal end of the STL 1300 (cuff 1350) may be implanted on the hypoglossal nerve or a branch of the hypoglossal nerve in the submandibular region, and the proximal end of the STL 1300 may be tunneled under the skin to the INS 1100. The RSL 1300 may be tunneled under the skin from the INS 1100 to the rib cage. The INS 1100 detects respiration via the RSLs 1200 using bio-impedance.

Stimulation Lead (STL)

Figure 2:
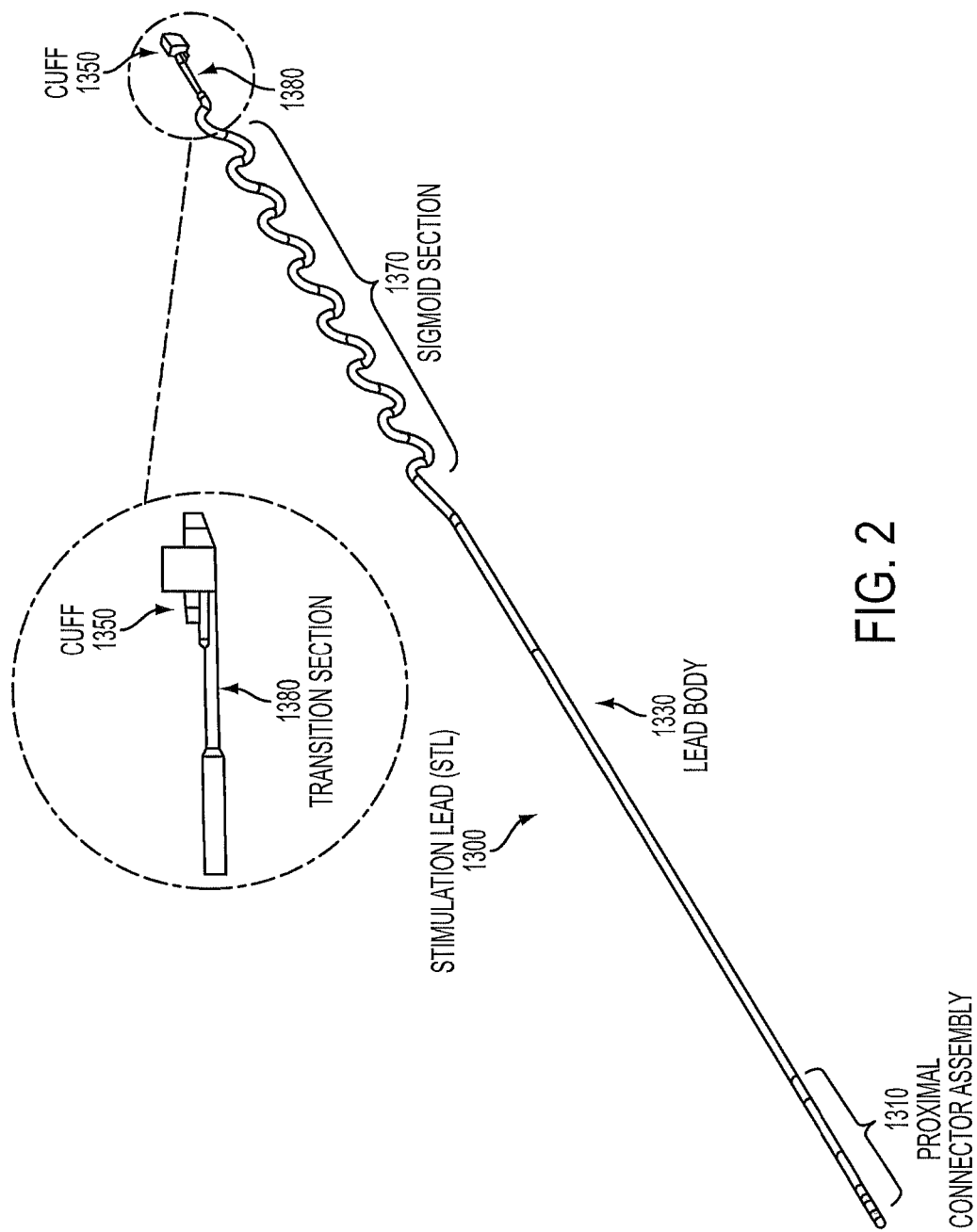
FIG. 2 is a perspective view of a stimulation lead for use in the system shown in FIG. 1, including a detailed view of the distal end of the stimulation lead.

FIG. 2 schematically illustrates the STL 1300 in more detail. The STL 1300 is designed to deliver the stimulation signal from the INS 1100 to the hypoglossal nerve and includes a proximal connector assembly 1310, a main tubular body 1330, and a distal cuff 1350. The main tubular body of the STL includes a sigmoid shaped section 1370 and a distal flexible transition section 1380 proximal of the cuff. The STL may have a nominal outside diameter of 0.062 inches to have minimal cosmetic impact, and an overall length of 17.7 inches (45 cm) (including cuff) to extend from the infraclavicular region (INS) to the submandibular region (hypoglossal nerve) and to accommodate anatomical variation.

The main tubular body 1330 of the STL 1300 is designed to withstand gross neck movement as well as mandibular movement and hypoglossal nerve movement caused by talking, chewing, swallowing, etc. To survive in this high fatigue environment, the main tubular body 1330 incorporates a highly compliant silicone jacket in the form of a sigmoid, and two conductors 1390 (one for cathode electrodes, one for anode electrodes) each comprising ETFE insulated MP35N multifilament cable disposed inside the jacket in the form of a bi-filar coil (not visible). This design provides high fatigue resistance and three-dimensional flexibility (bending and elongation).

Figure 3A:
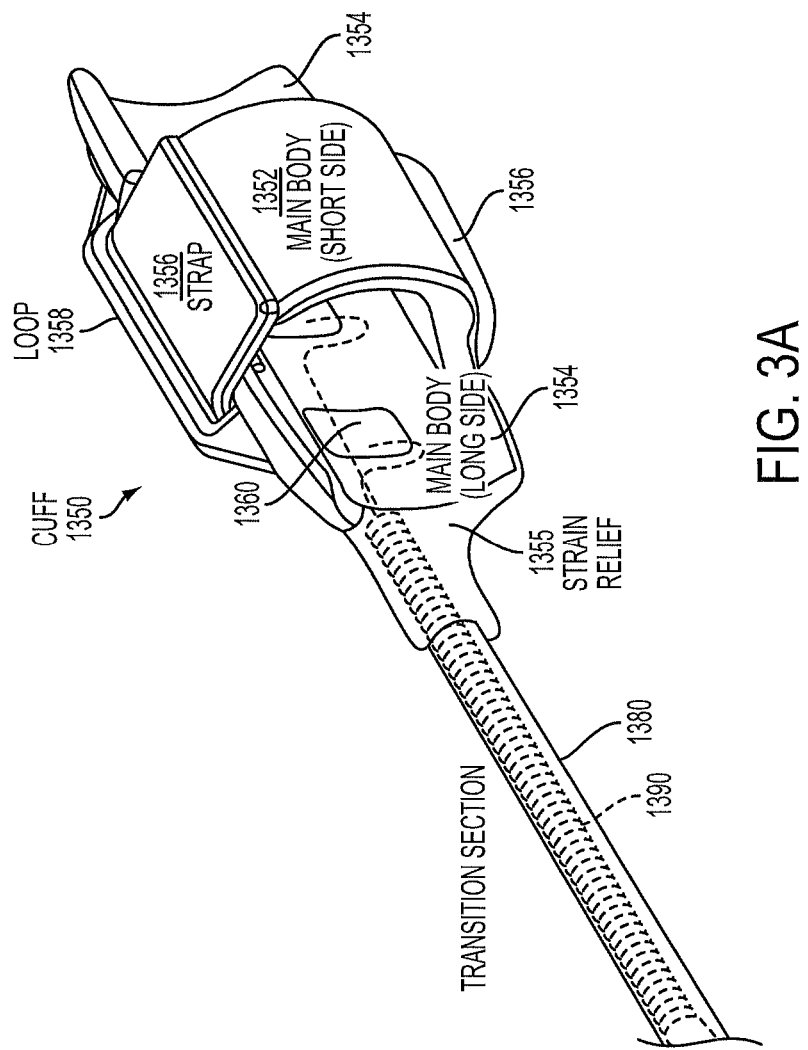
FIG. 3A is a detailed perspective view of the cuff of the stimulation lead shown in FIG. 2.
Figure 3B:
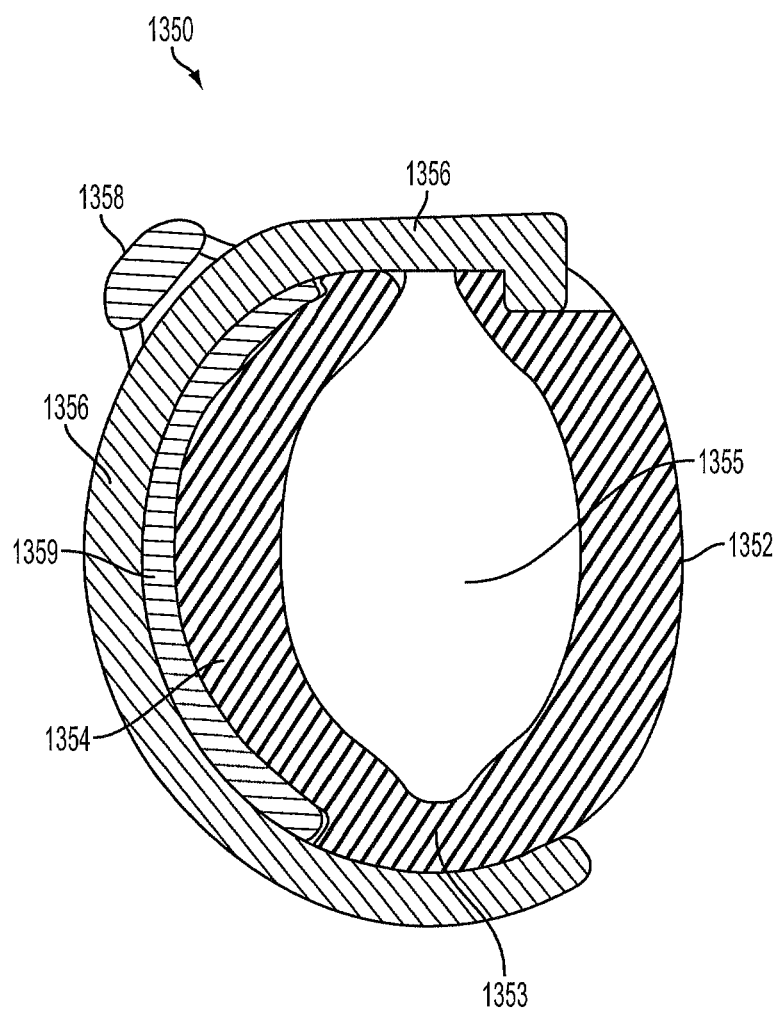
FIG. 3B is a lateral cross-sectional view of the cuff shown in FIGS. 2 and 3A.

The proximal connector assembly 1310 is designed to provide a reliable mechanical and electrical connection of the STL 1300 to the INS 1100. It has a number of strain relief elements that enable it to withstand handling during insertion and removal from the INS 1100, as well as adverse conditions encountered when implanted. The connector assembly 1310 includes two in-line stainless steel ring contacts (one for each conductor 1390) and two silicone ring seals. Set screws in the header of the INS 1100 bear down on the contacts, and together with the ring seals, provide a sealed mechanical and electrical connection to the INS 1100. More detailed views of the cuff 1350 are shown in FIGS. 3A and 3B, wherein FIG. 3A schematically illustrates the cuff 1350 in isometric view, and FIG. 3B schematically illustrates the cuff 1350 in cross-sectional view. The cuff 1350 has a hinged oval-shaped silicone body (collectively 1352 and 1354) to define an oval lumen 1355 that provides secure and gentle retention around the hypoglossal nerve. The cuff 1350 may be designed to fit the nerve very closely to minimize tissue growth between the electrode and nerve. Thus, the cuff may be available in two sizes to accommodate nerves of different diameter: a small size to accommodate nerves having a diameter of up to about 2.5-3.0 mm, and a large size to accommodate nerves having a diameter of up to 3.2-4.0 mm. At 3.0 mm nerve diameter, either size cuff will fit the nerve with minimal open space for tissue in-growth. Using a large cuff on a 2.5 mm nerve allows clearance between the nerve and electrode which promotes capsule formation. This may cause an increase in capture threshold but will not affect safety. Conversely, a small cuff placed on a large nerve minimizes electrode coverage around the nerve and may fall off with swelling. The short side 1352 (e.g., 4.0 mm long) of the cuff body fits between nerve branches and connective tissue on the deep side of the nerve, thereby minimization nerve dissection. The long side 1354 (e.g., 10.0 mm long) of the cuff body rests on the superficial side of the nerve (where few braches exist) and is connected to the transition section 1380 of the main lead body 1330.

A silicone strap 1356 is connected to and extends from the short side 1352 of the cuff body. A silicone top plate comprising an integral base portion 1359 and loop 1358 is attached to and covers the exterior surface of the long side 1354 of the cuff body. The strap 1356 freely slides through the loop 1358, and wraps around the long side 1354 of the cuff body. The strap 1356 is removed from the loop 1358 for placement of the cuff 1350 around the nerve and reinserted into the loop 1358 to hold the cuff 1350 on the nerve. A mark may be disposed on the strap 1356 of the small size cuff to indicate that the cuff is too small and that a larger size cuff should be used if the mark does not pass through the loop 1358. The cuff body readily expands along a hinge line 1353 (defined at the junction of the short side 1352 to the long side 1354) as well as other portions of the cuff 1350 structure. Expansion of the cuff body accommodates nerves of different diameters and nerve swelling after implantation, while the strap 1356 remains in the loop 1358 to retain the cuff 1350 on the nerve. In the event of excess nerve swelling (e.g., >50% increase in nerve diameter) or traction from the lead 1300 (e.g., as may accidentally occur during implantation), the strap 1356 pulls out of the loop 1358 and releases the cuff 1350 from the nerve to minimize the potential for nerve damage.

The cuff body carries four platinum-iridium electrodes 1360 (e.g., 2.0 mm$^2$ exposed area each for small cuff, 3.0 mm$^2$ exposed area each for large cuff), with one cathode electrode 1360 on the short side 1352, another cathode electrode 1360 (not visible) diametrically opposed on the long side 1354, and two anode electrodes 1360 guarding the cathode electrode 1360 on the long side 1354. This guarded dual cathode arrangement provides a more uniform electrical field throughout the cross-section of the nerve while minimizing electrical field outside of the cuff. One conductor 1390 may be connected to the cathode electrode 1360 on the long side, to which the other cathode electrode 1360 on the short side is connected by a jumper wire. Similarly, the other conductor 1390 may be connected to the distal anode electrode 1360, to which the proximal anode electrode 1360 is connected by jumper wire. With this arrangement, the cathode electrodes are commonly connected to one conductor 1390 and the anode electrodes are commonly connected to the other conductor 1390.

With the exception of the metal electrode contacts in the cuff, all external surfaces of the STL 1300 exposed to the body when implanted may comprise implantable grade polymers selected from the following: silicone, and fully cured silicone adhesive. The metal electrode contacts in the cuff may comprise implantable grade platinum-iridium and are secured to the silicone cuff body with silicone adhesive, for example.

Respiration Sensing Lead (RSL)

Figure 4A:
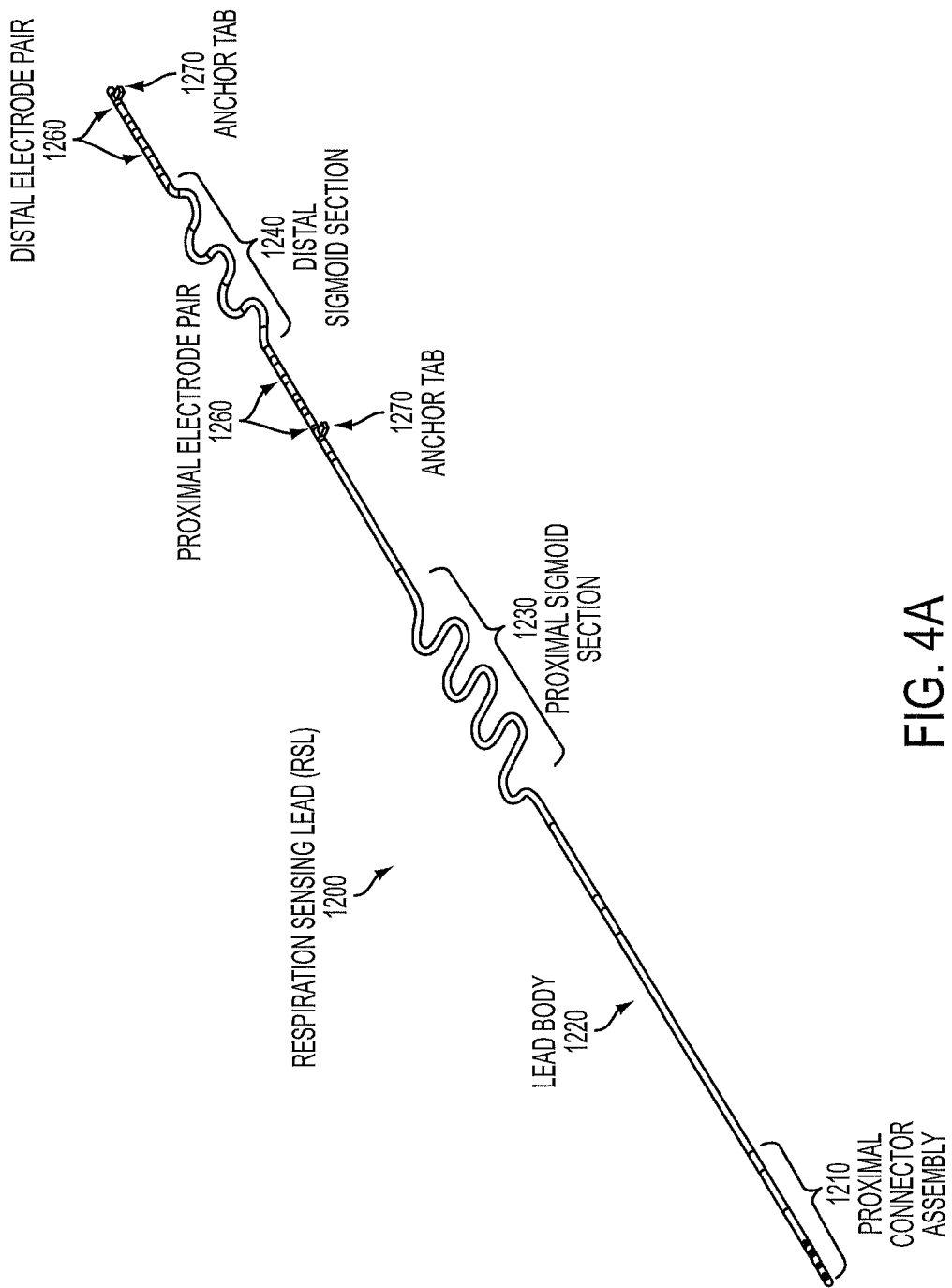
FIG. 4A is a perspective view of a respiration sensing lead for use in the system shown in FIG. 1.
Figure 4B:
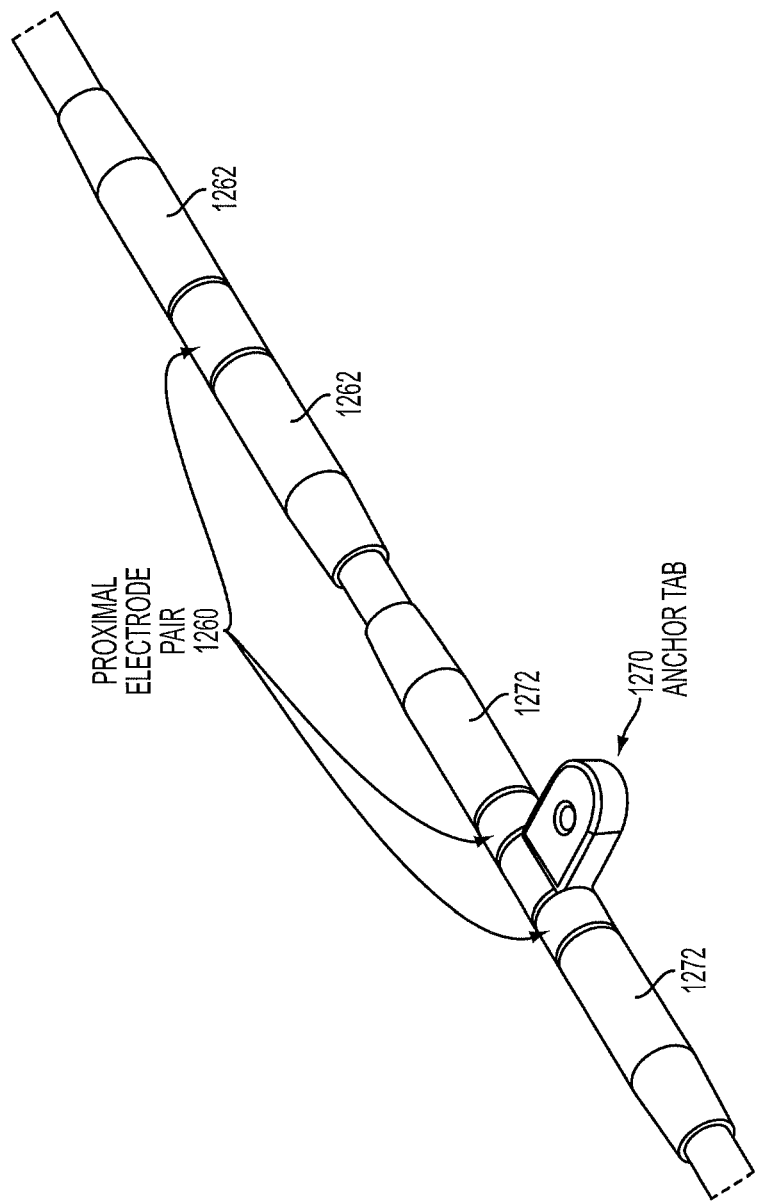
FIG. 4B is a detailed perspective view of the proximal electrode pair of the respiration sensing lead shown in FIG. 4A.

FIGS. 4A and 4B schematically illustrate the respiration sensing lead 1200 in more detail. The respiration sensing lead 1200 is designed to measure bio-impedance and includes a proximal connector assembly 1210, a main tubular body 1220, and two distal ring electrode pairs 1260. The main tubular body 1220 of the RSL 1200 includes a proximal sigmoid section 1230 and a distal sigmoid section 1240 between the electrode pairs 1260. The RSL 1200 may have a nominal outside diameter of 0.072 inches to have minimal cosmetic impact, and an overall length of 24.3 inches (61.6 cm) unstretched, 32.0 inches (81.3 cm) stretched to extend from the infraclavicular region (where the INS 1100 is implanted) to the right or left rib cage (where the RSLs 1200 may be implanted) and to accommodate anatomical variation.

The main tubular lead body 1220 of the RSL 1200 is designed to withstand thoracic movement due to flexion, extension, rotation and breathing. To withstand this environment, the main tubular body 1220 may include a flexible silicone jacket formed into two sigmoid sections 1230, 1240 and four conductors comprising small diameter ETFE insulated MP35NLT wires (not visible) disposed inside the jacket in the form of a quad-filar coil. The proximal sigmoid section 1230 isolates movement of the INS 1100 from the electrode pairs 1260 and accommodates anatomic variations in thoracic length. The distal sigmoid section 1240 allows adjustment in the distance between electrode pairs 1260 and reduces strain applied between the anchor tabs 1270, which may be secured with sutures to the underlying fascia when implanted. The proximal sigmoid 1230 section may have 3½ wavelengths with a peak-to-peak dimension of approximately 0.94 inches (2.4 cm) and an overall length of 5.5 inches (14.0 cm). The distal sigmoid 1240 section may have 2½ wavelengths with a peak-to-peak dimension of approximately 0.94 inches (2.4 cm) and an overall length of 5.5 inches (14.0 cm).

The two distal electrode pairs 1260 may comprise four electrodes total, and each may comprise MP35N rings having an exposed surface area of 28.0 mm$^2$, for example. As shown in FIG. 4B, tubular strain relief segments 1262 and 1272 may be disposed on the lead body on either side of each electrode 1260. Where the strain relief segments 1262 and 1272 are adjacent each other, a gap may be provided there between as shown in FIG. 4B or the segments may abut each other to avoid a stress concentration point. The anchor tab 1270 may be disposed over an electrode as shown in FIG. 4B leaving the proximal and distal extremities of the electrode exposed.

At any given time, the INS 1100 detects impedance along a vector, with each end of the vector defined by one active pair of electrodes 1260. In each active pair of electrodes 1260, one electrode delivers a small excitation current, and the other electrode monitors the corresponding change in voltage. The INS 1100 may also act as a current emitting and/or voltage sensing electrode. Changes in impedance are calculated by dividing the change in voltage by the excitation current, which correspond to movement of the diaphragm and lung to produce a signal indicative of respiratory activity.

The proximal connector assembly 1210 of the RSL 1200 is designed to provide a reliable mechanical and electrical connection of the RSL 1200 to the INS 1100. It has a number of strain relief elements that enable it to withstand handling during insertion and removal from the INS 1100, as well as adverse conditions encountered when implanted. The connector assembly 1210 may include four in-line stainless steel ring contacts (one for each conductor) and four silicone ring seals. Set screws in the header of the INS 1100 bear down on the contacts, and together with ring seals, provide a sealed mechanical and electrical connection to the INS 1100.

With the exception of the distal electrodes, all external surfaces of the RSL 1200 exposed to the body when implanted may comprise implantable grade polymers selected from the following: silicone, and fully cured silicone adhesive. The distal electrodes may comprise implantable grade MP35N and are sealed to the lead body with silicone adhesive, for example.

Figure 4C:
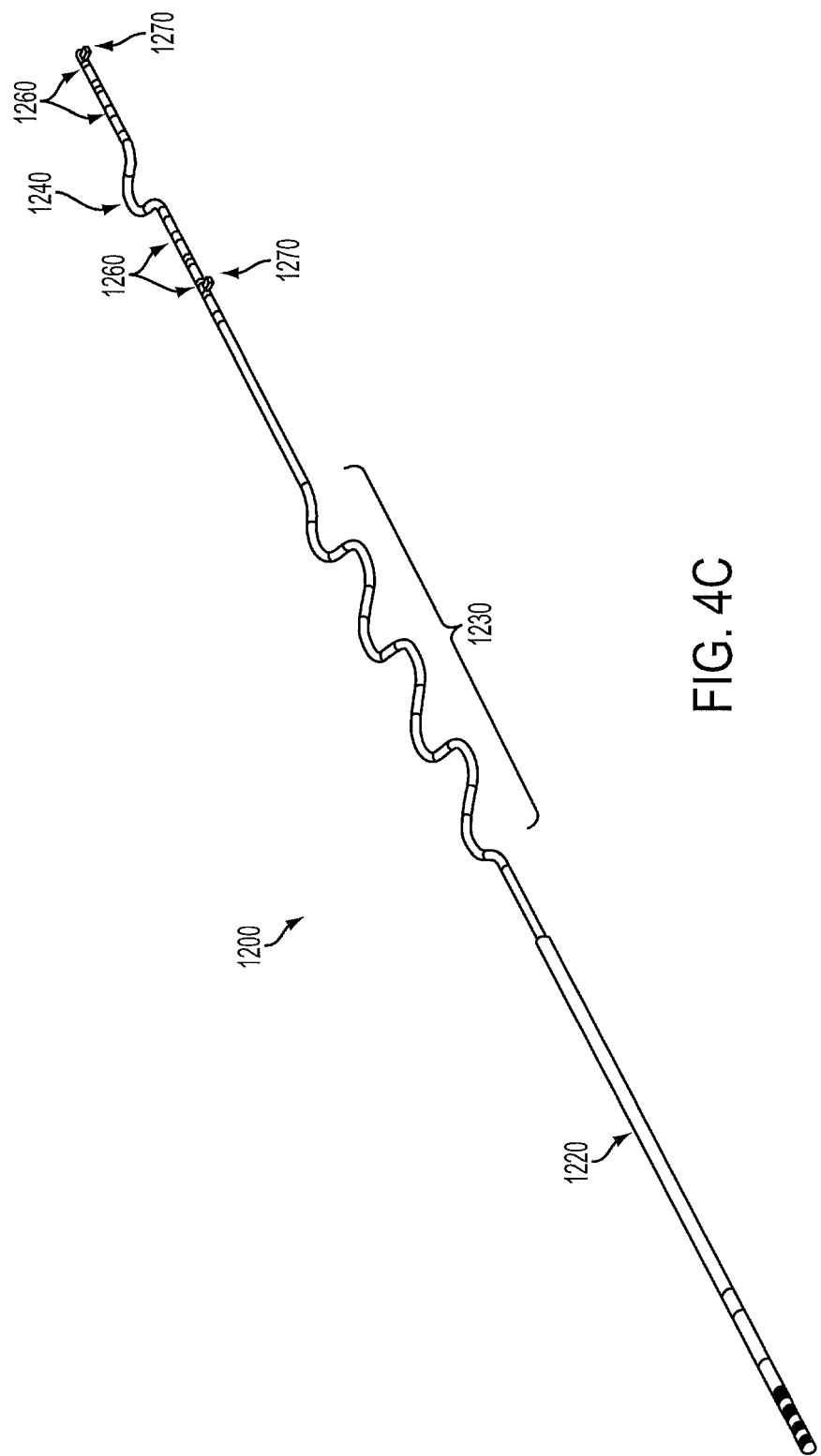
FIG. 4C is a perspective view of an alternative respiration sensing lead for use in the system shown in FIG. 1.

FIG. 4C schematically illustrates an alternative embodiment of the respiration sensing lead 1200. In this embodiment, the RSL 1200 may have a nominal outside diameter of 0.072 inches to have minimal cosmetic impact, and an overall length of 23.5 inches (59.7 cm) unstretched, 26.5 inches (67.2 cm) stretched. The proximal sigmoid 1230 section may have 3½ wavelengths with a peak-to-peak dimension of approximately 0.94 inches (2.4 cm) and an overall length of 5.5 inches (14.0 cm). The distal sigmoid 1240 section may have ½ wavelength with an amplitude of approximately 1.7 inches (4.4 cm) and an overall length of about 0.5 inches (1.3 cm).

Implantable Neurostimulator (INS)

Figure 5A:
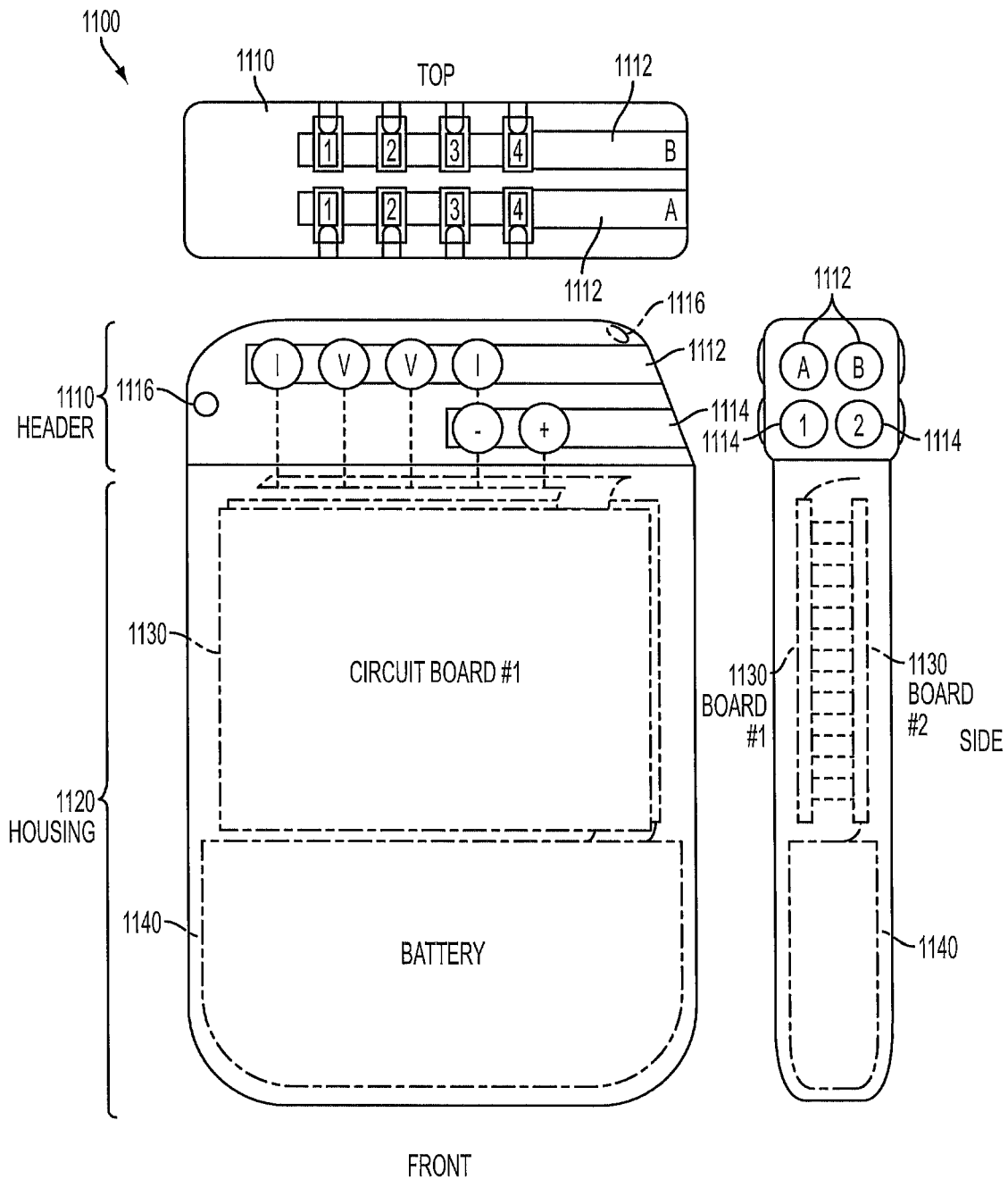
FIG. 5A shows front, side and top views of an implantable neurostimulator for use in the system shown in FIG. 1.

FIG. 5A schematically illustrates the INS 1100 in more detail, including a front view, a top view and a side view. The INS 1100 is similar in certain aspects to commercially available implantable pulse generators and implantable neurostimulators, which may be obtained from suitable manufacturers such as CCC Medical Devices (Montevideo, Uruguay). The INS 1100 generally includes a header 1110 for connection of the STL 1300 and RSLs 1200, and a hermetically sealed housing 1120 for containing the associated electronics 1130 and battery 1140 (e.g., WGL 9086).

The electronic circuitry 1130 contained in the INS 1100 enables telemetry communication with the programmer system 2100 and therapy controller 2500, detection of respiration via the RSLs 1200, determination of the trigger point for stimulation, and delivery of a controlled electrical stimulation signal (pulse train) via the STL 1300. The INS 1100 also records therapy data (device settings, respiration data, stimulation delivery data, etc.).

The header 1110 may comprise epoxy that is hermetically sealed to the housing 1120. The housing 1120 may comprise titanium. As mentioned in the context of respiration sensing, the housing 1120 may be used as an electrode for bio-impedance respiration measurement. For example, the housing 1120 may comprise a combination current emitting and voltage sensing electrode for respiration detection.

The header 1110 includes four ports: two RSL ports 1112 (labeled "sense" A and B) for receiving the proximal connectors of up to two RSLs 1200 and two STL ports 1114 (labeled "stim" 1 and 2) for receiving the proximal connectors of up to two STLs 1300. Each port that is configured to receive a STL 1300 includes two set screws (labeled "−" for cathode and "+" for anode) with associated set screw blocks and seals for mechanical and electrical connection to corresponding contacts on the proximal connector 1310 of the STL 1300. Similarly, each port that is configured to receive a RSL 1200 includes four set screws (two labeled "I" for current emitting electrodes and two labeled "V" for voltage sensing electrodes) with associated set screw blocks and seals for mechanical and electrical connection to corresponding contacts on the proximal connector 1210 of the RSL 1200. The header 1110 further includes two suture holes 1116 (only one is visible) for securing the INS 1100 to subcutaneous tissue such as muscle fascia using sutures when implanted in a subcutaneous pocket. As shown, approximate dimensions, component values and component configurations are given by way of example, not limitation.

The INS 1100 generates the stimulation output for delivery to the hypoglossal nerve by way of the STL 1300. For this purpose, the INS 1100 has two bipolar stimulation output channels, one channel corresponding to each STL port 1114, with each channel providing a pulse train of constant current with a frequency range of 20 to 50 Hz, a pulse width range of 30 to 215 µs, an amplitude range of 0.4 to 5.0 mA, and a stimulation duty cycle range of 41%-69%, by way of example, not limitation.

The INS 110 also generates the excitation signal and measures voltage by way of the RSLs 1200 for bio-impedance respiration detection. For this purpose, the INS 1100 also has two respiration sensing channels, one channel corresponding to each RSL port 1112, with each channel providing a small excitation current ("I") and measuring voltage ("V"). The excitation signal may comprise a 10 Hz biphasic constant current pulse, with the positive and negative phases of each biphasic pulse having an amplitude of 300 µA, a duration of 50 µs, and a charge of 15 nC. Changes in impedance ("Z") are calculated by dividing the change in measured voltage ("V") by the excitation current ("I"), which corresponds to movement of the diaphragm, lung, and other structures to produce a signal indicative of respiratory activity.

Figure 5B:
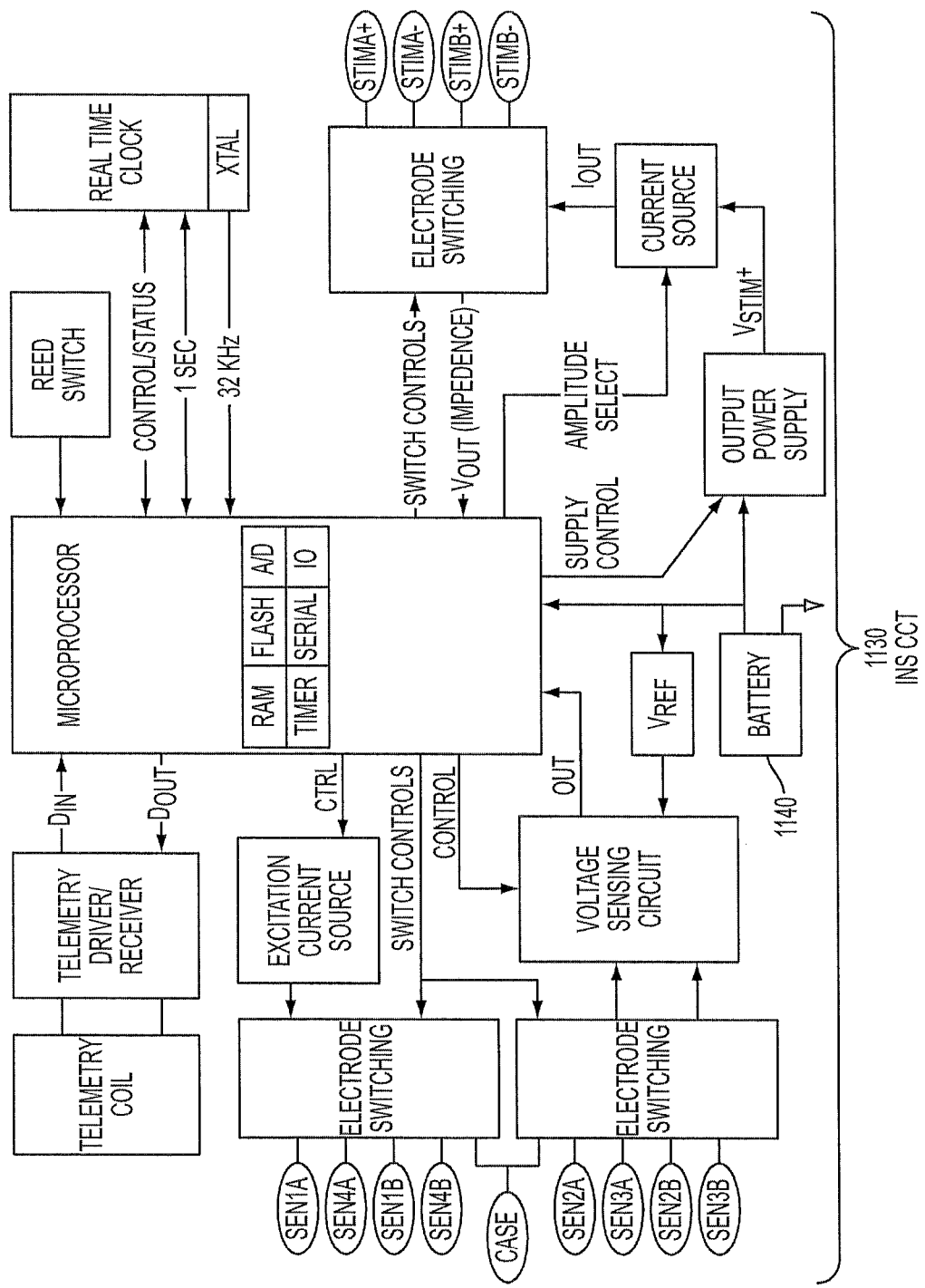
FIG. 5B is a schematic block diagram of electronic circuitry for use in the implantable neurostimulator shown in FIG. 5A.

With reference to FIG. 5B, a block diagram of an example of the INS circuit 1130 is shown schematically. The INS circuit 1130 utilizes a microprocessor to control telemetry communications with the programmer system 2100, operating the sensing circuits to monitor respiration via the RSLs 1200, controlling the delivery of output stimuli via the STLs 1300, monitoring the magnetically sensitive reed switch and the real-time clock. The microprocessor contains built-in support circuits (RAM, Flash Memory, Analog to Digital (A/D) Converter, Timers, Serial Ports and Digital IO) used to interface with the rest of the INS circuit 1130. The microprocessors. Two microprocessors communicating via a serial link may be used instead of one microprocessor, with the first microprocessor for telemetry communications, monitoring the magnetically sensitive reed switch and the real-time clock; and the second microprocessor for operating the sensing circuits and controlling the delivery of output stimuli.

The telemetry interface circuits consist of a tuned telemetry coil circuit and a telemetry driver/receiver circuit to allow pulse encoded communication between the external programmer system 2100 and the microprocessor. As an alternative to telemetry coils and an inductive link, RF antennae with associated circuitry may be used to establish a RF link to provide for arms-length telemetry. The reed switch provides a means for the INS 1100 to be controlled by using a magnet placed in close proximity thereto. The real-time clock provides the basic time base (32 KHz) for the INS circuit 1130 as well as a clock (year, day, hour, minute, second) which can be used to control the scheduled delivery of therapy. The clock is also used to time-stamp information about the operation of the system that is recorded on a nightly basis.

The respiratory sensing circuits comprise two main parts: the excitation current source (output) and the voltage sensing circuit (input). As will be described in more detail hereinafter, respiration is detected via the RSLs 1200 using a 4-wire impedance measurement circuit, where an excitation current is driven through a pair of electrodes, and the resulting voltage is measured on a separate pair of electrodes. Electrode switching circuits (one for each RSL 1200) allows the INS 1100 to monitor one of several different vectors from the two separate 4 electrode RSLs 1200. The INS housing 1120 may also be used as both an excitation and sensing electrode. The excitation current circuit delivers biphasic pulses of low level (300 uA) current to the selected electrode pair every 100 ms during sensing. The voltage sensing amplifier circuit synchronously monitors the voltage produced by the excitation current on the selected electrode pair. The resulting output signal is proportional to the respiratory impedance (0.2Ω to 10Ω) and is applied to the A/D circuit in the microprocessor for digitization and analysis.

The stimulation output circuits deliver bursts of biphasic stimulation pulses to either STL 1300. These bursts may be synchronized to the sensed respiratory waveform. The stimulation output circuits include an electrode switching network, a current source circuit, and an output power supply. The electrode switching network allows selection of the stimulation output channel (pair A or B), each corresponding to a STL 1300. The electrode switching network also allows for a charge balancing cycle following each stimulation pulse during which the outputs are connected together with no applied output pulse. The timing and polarity of the pulse delivery is provided by control outputs of the microprocessor. The microprocessor selects the amplitude (e.g., 0.5 mA to 5 mA) of the output current from the current source circuit which is applied through the switching network. The output power supply converts battery voltage to a higher voltage (e.g., 5V to 13V) which is sufficient to provide the selected current into the load impedance of the STL 1300. The microprocessor measures the voltage output from the electrode switching network resulting from the delivered current and the load impedance. The microprocessor divides the output voltage by the output current resulting in a measure of the load impedance (600Ω to 2500Ω) which can be an indicator of integrity of the STL 1300.

Figure 6A:
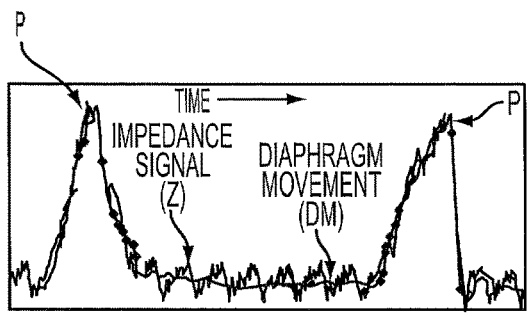
FIGS. 6A, 6B, 6C and 6D illustrate a bio-impedance signal, the corresponding physiological events, and trigger algorithms for use in the system shown in FIG. 1.

With reference to FIG. 6A, the bio-impedance respiration signal ("Z"), which is generated by dividing the change in measured voltage ("V") by the excitation current ("I"), tracks with diaphragm movement (DM) over time and therefore is a good measure of respiratory activity, and may be used to measure respiratory effort, respiratory rate, respiratory (tidal) volume, minute volume, etc. If the excitation current (I) is constant or assumed constant, then the bio-impedance (Z) is proportional to the measured voltage (V), and thus the voltage (V) may be used as a surrogate for bio-impedance (Z), thereby eliminating the division step. As used in this context, diaphragm movement includes movements and shape changes of the diaphragm and adjacent tissue that occur during normal breathing and during obstructed breathing. The (positive or negative) peak (P) of the impedance signal (Z) corresponds to the end of the inspiratory phase and the beginning of the expiratory phase. If the signal is normal (as shown), the positive peak is used; and if the signal is inverted, the negative peak is used. The beginning of the inspiratory phase occurs somewhere between the peaks and may not be readily discernable. Thus, the impedance signal provides a reliable fiducial (P) for end-inspiration and begin-expiration (also called expiratory onset), but may not provide a readily discernable fiducial for begin-inspiration (also called inspiratory onset). Therefore, algorithms described herein do not rely on begin-inspiration (or inspiratory onset) for triggering stimulation as proposed in the prior art, but rather use a more readily discernable fiducial (P) corresponding to begin-expiration (or expiratory onset) in a predictive algorithm as described below. Other non-predictive (e.g., triggered) algorithms are described elsewhere herein.

In people without OSA, the hypoglossal nerve usually activates approximately 300 ms before inspiration and remains active for the entire inspiratory phase. To mimic this natural physiology, it is desirable to deliver stimulation to the hypoglossal nerve during the inspiratory phase plus a brief pre-inspiratory period of about 300 ms. As mentioned previously, a reliable fiducial for the beginning of the inspiratory phase may not be available from the impedance signal, and a reliable fiducial for the pre-inspiratory period may not be available either. However, there are reliable fiducials for the beginning of the expiratory phase (peak P) which may be used to trigger stimulation to cover the inspiratory phase plus a brief pre-inspiratory period.

Accordingly, an algorithm is used to predict respiratory period and determine stimulation trigger time. The predictive algorithm is contained in software and executed by a microprocessor resident in the INS circuitry 1130, thus enabling the INS 1100 to generate stimulation synchronous with inspiration.

Figure 6B:
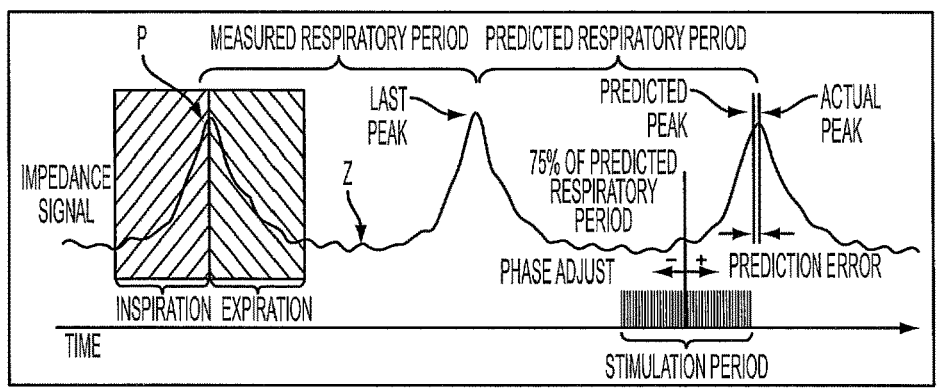

One example of a predictive algorithm is illustrated in FIG. 6B. In this example, the stimulation period is centered about a percentage (e.g., 75%) of the predictive respiratory period. The predictive algorithm uses historical peak data (i.e., begin-expiration data) to predict the time to the next peak, which is equivalent to the predicted respiratory period. The stimulation period is centered at 75%, for example, of the predicted respiratory time period. Thus, the stimulation trigger point is calculated by predicting the time to the next peak, adding 75% of that predicted time to the last peak, and subtracting ½ of the stimulation period (trigger time=time of last peak+75% of predicted time to next peak−½ stimulation period). A phase adjustment parameter (range: −1500 ms to +500 ms, for example) permits the stimulation period to be biased early or late. A default setting (e.g., −500 ms) of the phase adjustment parameter moves the stimulation period early relative to the anticipated start of inspiration.

Figure 6C:
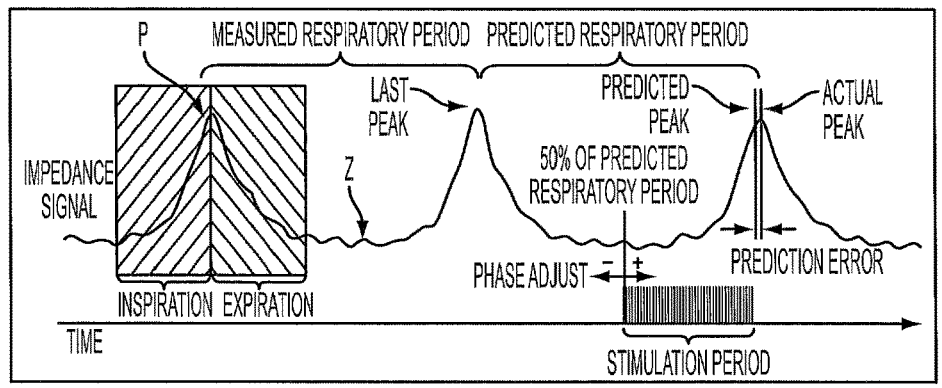

Another example of a predictive algorithm is illustrated in FIG. 6C. This example differs for the example illustrated in FIG. 6B in that the stimulation period is initiated (not centered) at a percentage (e.g., 50%) of the predicted respiratory period. However, the two examples have essentially equivalent results for a duty cycle of 50%. As in the prior example, the predictive algorithm uses historical peak data (i.e., begin-expiration data) to predict the time to the next peak, which is equivalent to the predicted respiratory period. The stimulation period may start at 50%, for example, of the predicted time period. Thus, the stimulation trigger point is calculated by predicting the time to the next peak and adding 50% of that predicted time to the last peak (trigger time=time of last peak+50% of predicted time to next peak). A phase adjustment parameter (range: −1500 ms to +500 ms, for example) permits the stimulation period to be biased early or late. A default setting (e.g., −500 ms) of the phase adjustment parameter moves the stimulation period early relative to the anticipated start of inspiration.

Figure 6D:
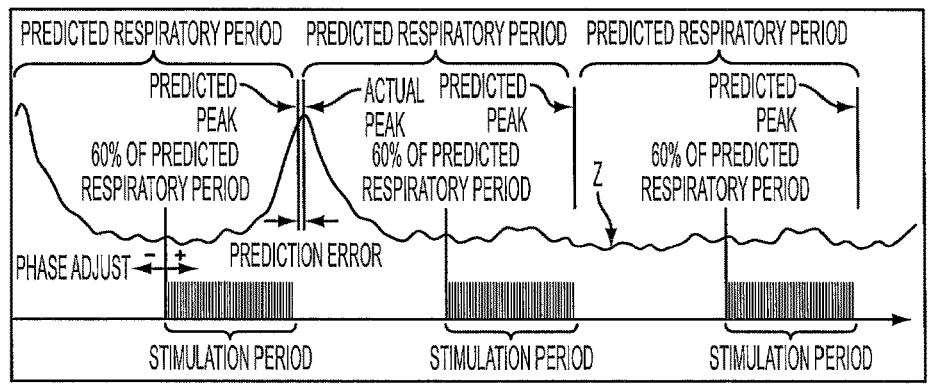

A feature common to the predictive algorithms is illustrated in FIG. 6D. This feature provides a sequence of predicted respiratory periods in case the respiration impedance signal ("Z") is temporarily lost (e.g., due to change in respiratory effort). Until a subsequent respiratory peak is detected, stimulation parameters which are based on the measured respiratory period (e.g., stimulation period) are unchanged. Thus, stimulation timing remains synchronous to the last detected peak.

The stimulation duty cycle may vary to meet efficacy and safety requirements. Generally, the stimulation duty cycle is used to determine the stimulation period as a percentage of the predicted respiratory period (stimulation period=duty cycle×predicted respiratory period). After a stimulation period is started, stimulation continues until the end of the stimulation period as set by the stimulation duty cycle, or until the next actual peak is detected, whichever occurs first.

Note that the result of the algorithm illustrated in FIG. 6B is the same as the result of the algorithm illustrated in FIG. 6C for a stimulation duty cycle of 50%.

The stimulation duty cycle may be fixed or adaptive. In the fixed mode, the stimulation duty cycle is set using to programmer system 2100 to a fixed value. This fixed value may be increased when the respiratory signal is lost. In adaptive mode, the duty cycle is allowed to vary as a function of a characteristic of respiration. For example, the adaptive duty cycle may increase with an increase in respiratory period variability or with the loss of respiratory signal. Thus, in some instances, the stimulation duty cycle may run above normal (e.g., above 50% to 60%) to achieve a better likelihood of covering the inspiratory phase. Because above normal stimulation duty cycle may result in nerve and/or muscle fatigue if prolonged, it may be desirable to offset above-normal stimulation periods with below-normal stimulation periods to result in a net normal duty cycle. For example, if a X % stimulation duty cycle is defined as normal and the adaptive mode results in a period T1 where the stimulation duty cycle runs Y % more than X %, the above-normal stimulation period may be proportionally offset by a below-normal stimulation period T2 where the stimulation duty cycle runs Z % less than X % to satisfy the equation Y×T1=Z×T2. This equation is approximate and may vary slightly depending on the averaging technique used. Other offset methods may be used as an alternative.

The following stimulation duty cycle parameters are given by way of example, not limitation. In fixed mode, the maximum stimulation duty cycle may be set from 41% to 69% in 3% increments, and the default setting may be 50%. In adaptive mode, the stimulation duty cycle for a respiratory period may vary from 31% to 69% in 3% increments, and the maximum running average may be set to 53%. As mentioned above, the adaptive mode allows the duty cycle to increase with respiratory period variability, for example, and the stimulation duty cycle may run in excess of 53% for a limited period of time, but those periods are proportionally offset by periods where the stimulation duty cycle runs less than 53% (e.g., according to an exponentially weighted moving average). For example, an adaptive duty cycle set to 69% would run at that level for no longer than 5 to 7 minutes before being offset by a lower stimulation duty cycle at 47% to result in a running average of 53%.

Programmer System

Figure 7A:
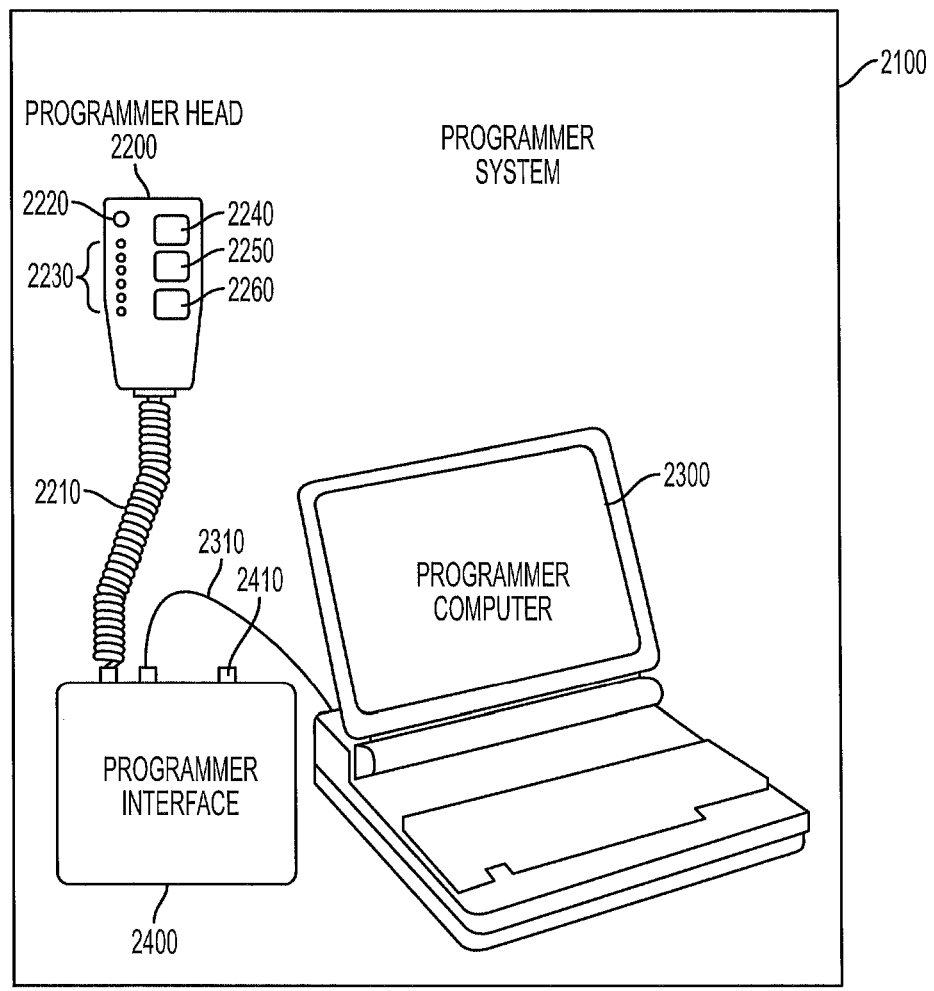
FIG. 7A is a schematic illustration of the programmer system for use in the system shown in FIG. 1.

As shown schematically in FIG. 7A, the programmer system 2100 includes a computer 2300, a programmer interface 2400 and a programmer head 2200. The programmer interface 2400 and programmer head 2200 are similar in certain aspects to commercially available programmers, which may be obtained from suitable manufacturers such as CCC Medical Devices (Montevideo, Uruguay). The programmer head 2200 is connected to the programmer interface 2400 via a flexible cable 2210, and the programmer interface 2400 is connected to the computer 2300 via a USB cable 2310. Cable 2210 may be coiled as shown or straight. The programmer system 2100 wirelessly communicates with the INS 1100 via a wireless telemetry link (e.g., 30 KHz) utilizing an antenna and associated circuitry in the programmer head 2200. The programmer interface 2400 provides analog to digital conversion and signal processing circuitry allowing the computer 2300 to control and program the INS 1100 via the programmer head 2200. The programmer head includes a power indication LED 2220, a signal strength LED array (signal strength to/from INS 1100), an interrogate button 2240 (to download data from INS 1100), a program button 2250 (to upload data/commands to the INS 1100) and a therapy-off button 2260 (to stop therapy/stimulation output from the INS 1100). The computer 2300 may comprise a conventional laptop computer with software to facilitate adjustment of a variety of INS 1100 parameters, including, for example: stimulation parameters (stimulation pulse amplitude, stimulation pulse frequency, stimulation pulse width, stimulation duty cycle, etc.); respiration sensing algorithm parameters; stimulation trigger/synchronisation algorithm parameters, therapy delivery schedule, and various test functions.

Figure 7B:
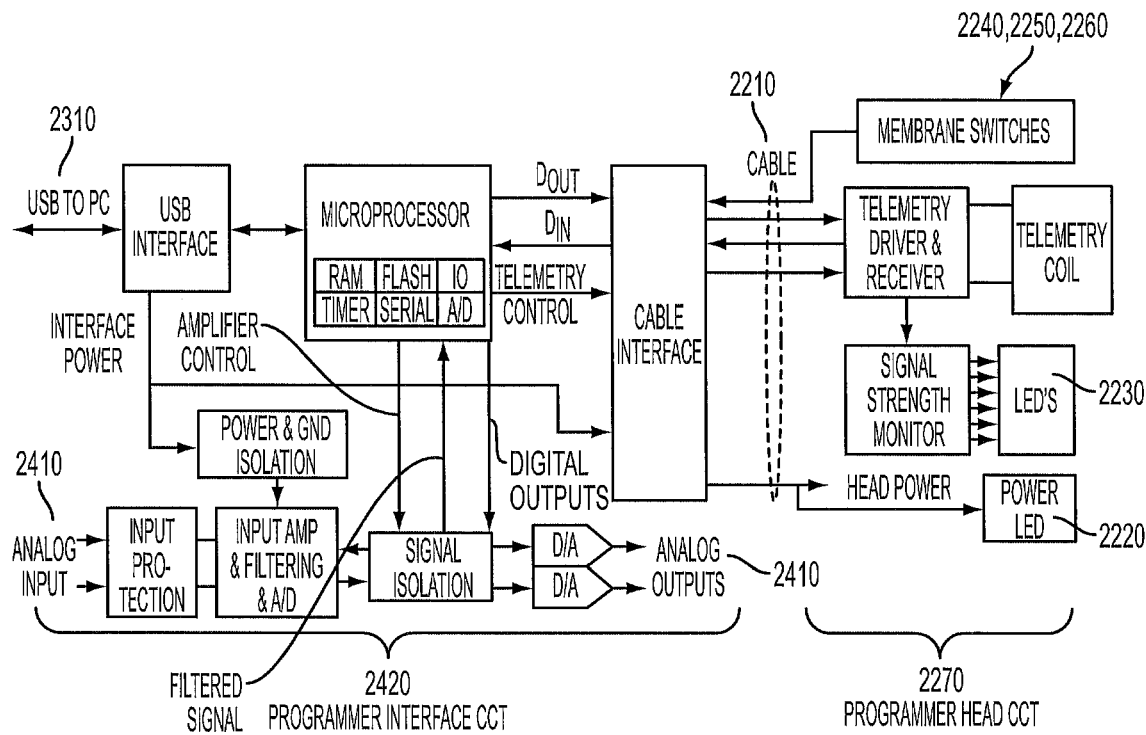
FIGS. 7B and 7C are schematic block diagrams of electronic circuitry for use in the programmer system for shown in FIG. 7A.

With reference to FIG. 7B, a block diagram of example circuits 2420/2270 for the programmer interface 2400 and the programmer head 2200 are shown schematically. The programmer interface circuit 2420 is controlled by a microprocessor having a standard set of peripherals (RAM, Flash, Digital I/O, Timers, Serial Ports, A/D converter, etc). The microprocessor communicates with a standard personal computer (PC) 2300 through a Universal Serial Bus (USB) interface. Commands and data are passed from the computer 2300 to/from the microprocessor via the USB interface and cable 2310. The USB interface also provides DC power for the programmer interface circuit 2420 and the programmer head circuit 2270 via cable 2210. The microprocessor controls the cable interface leading to the programmer head circuit 2270 via cable 2210. The programmer head circuit 2270 contains telemetry driver and receiver electronics that interface to the telemetry coil. The telemetry coil is designed to inductively couple signals from the programmer head circuit 2270 to the coil in the INS circuit 1130 when the programmer head 2200 is placed over the INS 110 with the coils aligned. As an alternative to telemetry coils and an inductive link, RF antennae with associated circuitry may be used to establish a RF link to provide for arms-length telemetry. The programmer head circuit 2270 also contains electronics that monitor the signal strength as received from the INS 1100. The outputs of the signal strength electronics drive display LED's for the user. Another LED indicates that power is available. The programmer interface microprocessor controls and receives analog input signals from an isolated sensor interface. The power and ground for the sensor interface are derived from the USB power input, but provide DC isolation for this circuitry to prevent leakage currents from flowing through any patient connections that may be present at the sensor inputs. The sensor inputs are protected against external high voltages (i.e. defibrillation protection). The sensor input signals are amplified and filtered appropriately for the sensor type. The amplifier gain and filter characteristics may be controlled by microprocessor. The signals to/from the amplifier circuit are DC isolated to prevent leakage currents from flowing through any patient connections that may be present at the sensor inputs. The sensor signals are digitized by the microprocessor and are transmitted through the USB link to the PC along with the telemetered signals from the INS 1100.

Figure 7C:
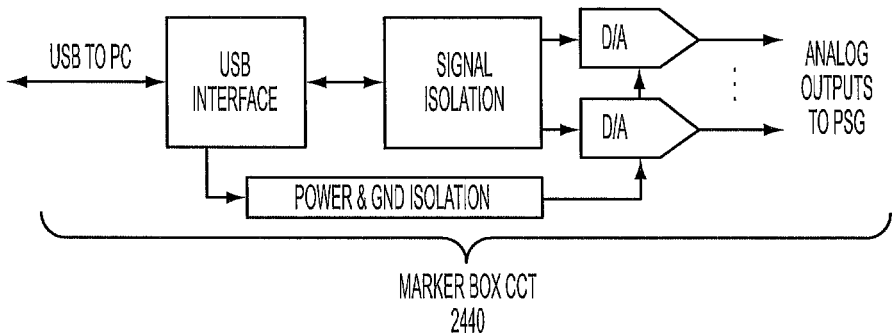

With reference to FIG. 7C, a block diagram of example circuit 2440 for the marker box 2430 is shown schematically. Generally, marker box 2430 and associated circuitry 2440 replace the D/A circuits and analog outputs 2410 of programmer interface circuit 2420 shown in FIG. 7B providing for the alternative arrangement illustrated in FIG. 10B. The marker box circuit 2440 is separately connected to a Universal Serial Bus (USB) port of the programmer computer 2300 via a USB cable. The USB interface also provides DC power for the marker box circuit 2440 via the USB cable. The power and ground for the marker box circuit 2440 are derived from the USB power input, but provide DC isolation for this circuitry to prevent leakage currents from flowing through any equipment that may be connected to the patient. Analog marker output data signals are transmitted from the PC 2300 to control the digital to analog (D/A) converter outputs. These analog output signals may be connected to standard PSG recording equipment 2800. Signals from the INS 1100 (such as sensed respiration impedance and stimulation output amplitude) can be represented by these outputs to allow simultaneous recording with other standard PSG signals (flow, belts, EMG/ECG, etc).

Therapy Controller

Figure 8A:
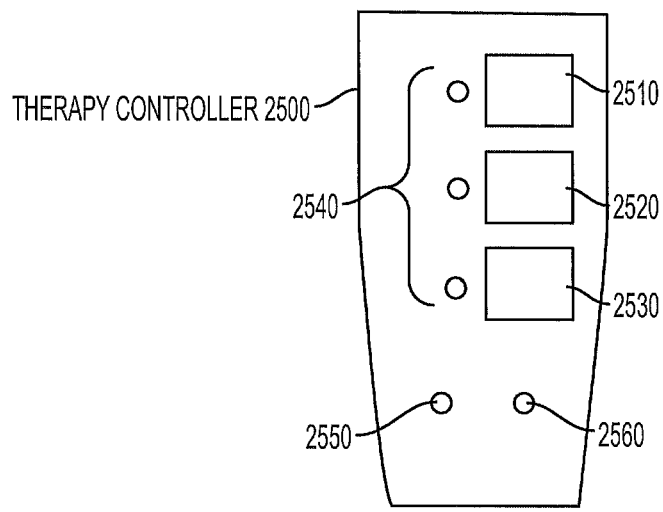
FIG. 8A is a schematic illustration of the therapy controller for use in the system shown in FIG. 1.

As shown schematically in FIG. 8A, the therapy controller 2500 may be used by the patient to control limited aspects of therapy delivery. The therapy controller 2500 is similar in certain aspects to commercially available patient controllers, which may be obtained from suitable manufacturers such as CCC Medical Devices (Montevideo, Uruguay). The therapy controller 2500 houses a battery, an antenna, and associated circuitry (not visible) to control limited aspects of therapy delivery via a wireless telemetry link (e.g., 30 KHz) with the INS 1100. Therapy is normally set for automatic delivery according to a predefined schedule (set by physician using the programmer during titration) but may also be operated in a manual mode. The therapy controller has a user interface including start button 2510 (to start therapy delivery), a stop button 2520 (to stop therapy delivery) and a pause button (to pause therapy delivery), each with associated LED indicators 2540 which flash when the corresponding button is depressed and illuminate steadily when the command is received by the INS 1100. The user interface also includes a schedule set LED 2550 that illuminates if a therapy delivery schedule has been programmed, and a contact physician LED 2560 that illuminates in the event of a low battery or a malfunction requiring a physician visit.

Figure 8B:
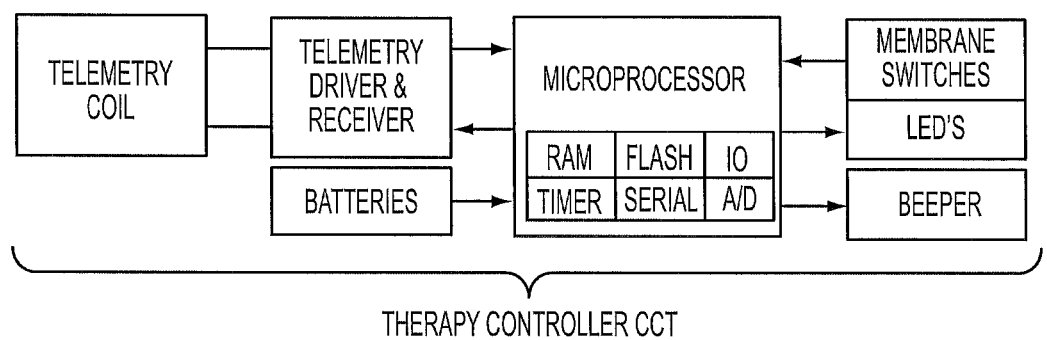
FIG. 8B is a schematic block diagram of electronic circuitry for use in the therapy controller shown in FIG. 8A.

With reference to FIG. 8B, a block diagram of an example circuit for the therapy controller 2500 is shown schematically. The therapy controller circuit 2570 includes a battery powered microprocessor having a standard set of peripherals (RAM, Flash, Digital I/O, Timers, Serial Ports, A/D converter, etc). The microprocessor operates in a low power mode to conserve battery power. The microprocessor controls the telemetry driver and receiver electronics that interface with the telemetry coil. The telemetry coil is designed to inductively couple signals to the INS telemetry coil when aligned. The microprocessor monitors the membrane switches and reacts to switch closures by activating display LED's and initiating telemetry commands to the INS. After communicating with the INS, status information can be displayed to the user. The microprocessor also controls a beeper which can provide audio feedback to the user when buttons are pressed and to indicate the success or failure of communications with the INS.

Magnet

Figure 9:
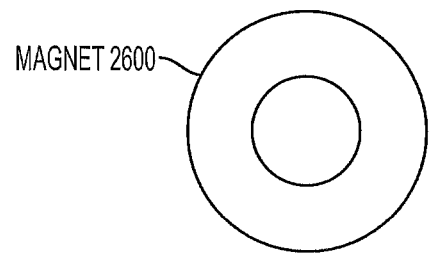
FIG. 9 is a top view of a magnet for use in the system shown in FIG. 1.

As schematically shown in FIG. 9, an annular magnet 2600 may be provided to the patient to deactivate the INS 1100 in the event the therapy controller 2500 is not available or functioning. The magnet 2600 may comprise a permanent annular-shaped magnet made of ferrite strontium material coated with epoxy. The magnet 2600 may produce a strong field of 90 Gauss at 1.5 inches from the surface of the magnet along the centerline of the hole. The magnet 2600 may be used (or carried by) the patient in case of emergency. When temporarily (2 seconds or more) placed over the implanted INS 1100 on the skin or clothing, the magnet 2600 disables current and future therapy sessions. Although therapy sessions are disabled by the magnet 2600, all other functions of the INS 1100 may remain enabled including telemetry communication with the programmer system 2100 and therapy controller 2500. Therapy sessions may be re-enabled using the programmer system 2100. The therapy controller 2500 may also re-enable therapy sessions if the therapy controller 2500 has been authorized by the programmer system 2100 to do so.

Interface with PSG Equipment

Figure 10A:
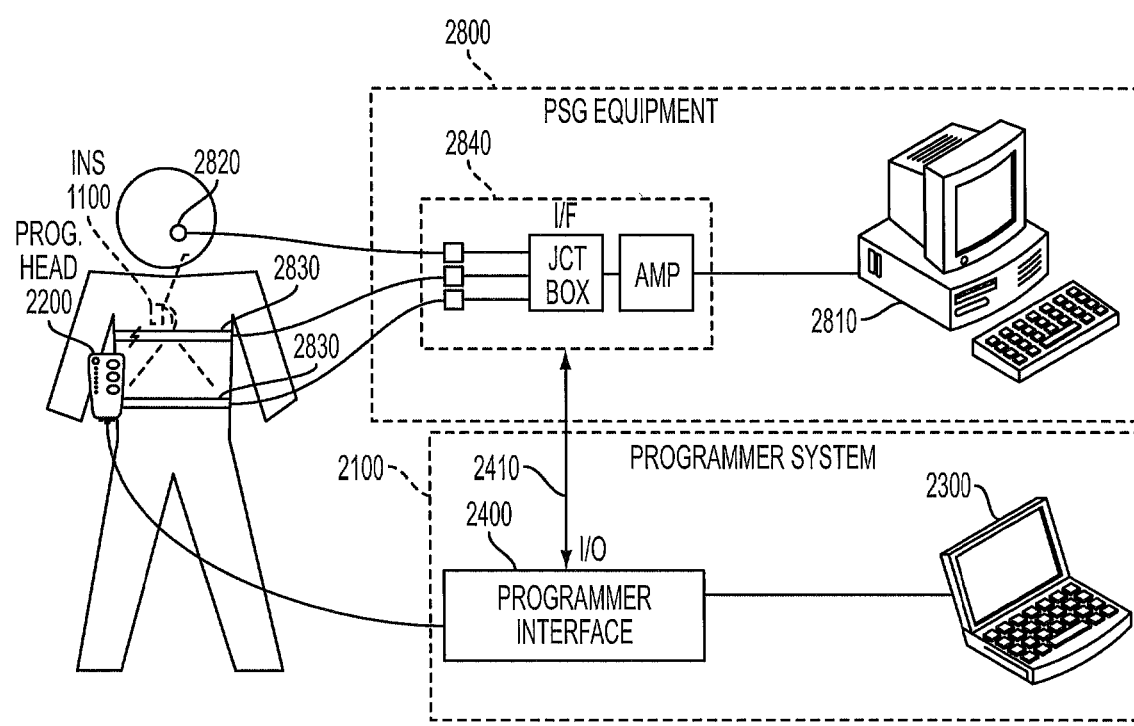
FIG. 10A is a schematic illustration of an interface of the system shown in FIG. 1 and polysomnographic equipment as may be used in a sleep study for therapy titration or therapy assessment, for example.
Figure 10B:
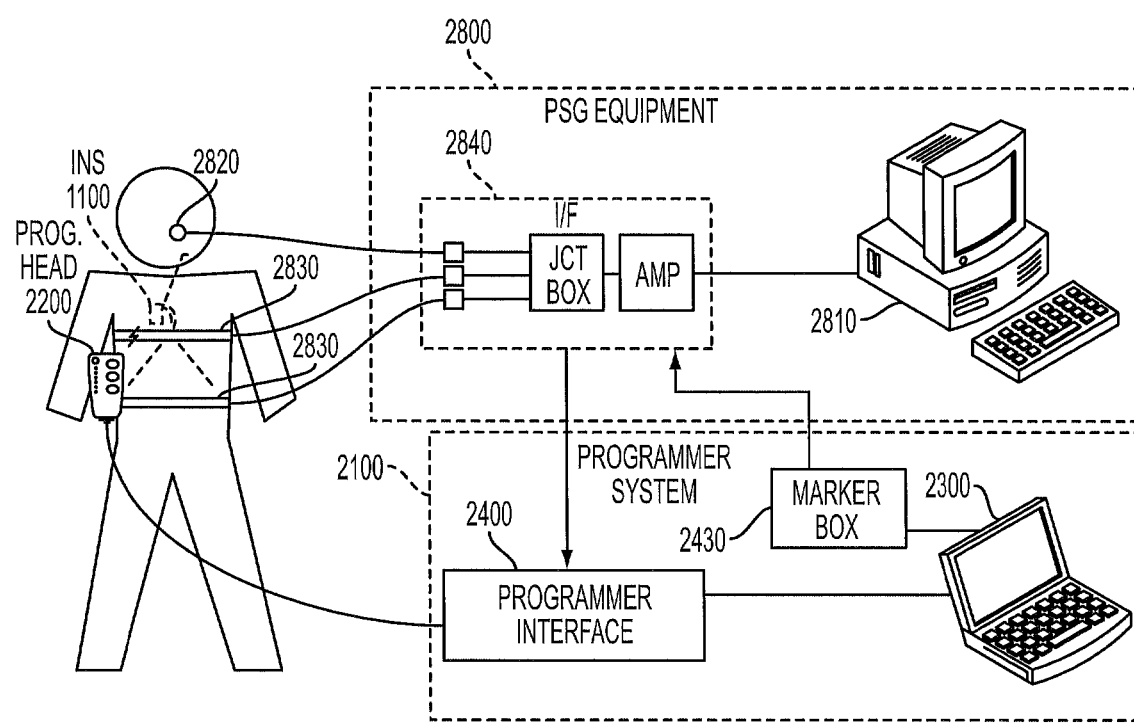
FIG. 10B is a schematic illustration of an alternative interface of the system shown in FIG. 1.

The programmer interface 2400 may include an input/output (I/O) link 2410 to allow connection to polysomnographic (PSG) equipment 2800 as schematically shown in. FIG. 10A. Typical PSG equipment 2800 includes a computer 2810 connected to a plurality of sensors (e.g., airflow sensor 2820, respiratory effort belts 2830) via interface hardware 2840. The I/O link 2410 may be used in a number of different ways. For example, analog data signals from the PSG equipment 2800 may be downloaded to the computer 2300 of the programmer system 2100 to record and/or display PSG data (e.g. airflow) together with therapy data. Alternatively or in addition, digital data signals from the INS 1100 and/or the programmer system 2100 may be uploaded to the computer 2810 of the PSG equipment 2800 to record and/or display therapy data (e.g., stimulation and/or respiration data) together with PSG data. The circuitry corresponding to I/O link 2410 may be incorporated into the programmer interface 2400 as shown in FIG. 10A, or may be incorporated into a separate marker box 2430 as shown in FIG. 10B.

Synchronizing data from the sensors 2820/2830 of the PSG equipment 2800 with data from the INS 1100 via the programmer system 2100 may be beneficial to facilitate therapy titration and efficacy measurement. Although the programmer system 2100 and the PSG equipment 2800 may be directly connected by I/O link 2410, transmission delay in each system may result in asynchrony. Data synchronization between the systems may be addressed in a number of different ways. For example, if the delays in each system are relatively fixed and below an acceptable threshold (e.g., 0.5 to 1.0 second), no synchronization step need be taken. If the delays in each system are relatively fixed but above an acceptable threshold (e.g., above 0.5 to 1.0 second), data from the system with less delay may be offset (delayed) by a fixed time value to align with data from the system with more delay. As an alternative, a timing signal (e.g., from a clock signal generator separate from or integral with one of the systems) may be input into the PSG equipment 2800 and programmer system 2100 to allow time stamped data independently collected by each system to be merged and synchronized by post processing.

Treatment Overview

Figure 11A:
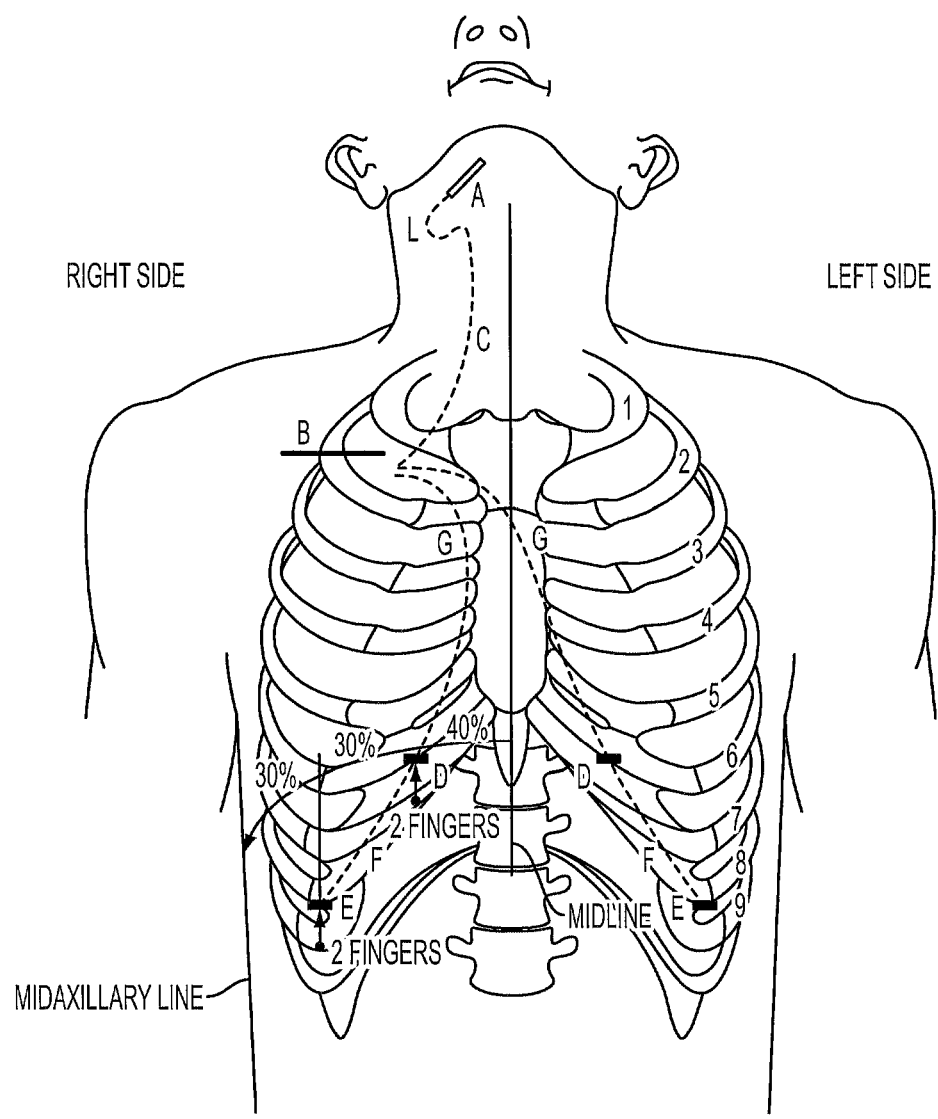
FIGS. 11A and 11D are anatomical illustrations showing the incision sites and tunneling paths that may be used for implanting the internal components shown in FIG. 1.

FIG. 11A schematically illustrates the incision sites (solid thick lines) and tunneling paths (dotted lines) for implanting the INS 1100, STL 1300 and RSLs 1200. The implant procedure may be performed by a surgeon (e.g., otolaryngologist) in a 1-2 hour surgical procedure with the patient under general anesthesia, for example. In general, the implant procedure involves placing the cuff 1350 of the SU 1300 on the hypoglossal nerve via a submandibular dissection, and tunneling the lead body 1330 and sigmoid section 1370 of the STL 1300 subcutaneously down the neck to the INS 1100 in a subcutaneous pocket in the infraclavicular region. From the infraclavicular pocket, the RSLs 1200 may be tunneled subcutaneously toward midline and then laterally along the costal margins.

After a healing period of a few weeks, the patient returns to the sleep lab where a sleep technician, under the supervision of a certified sleep physician (e.g., pulmonologist), uses the programmer system 2100 to program the INS 1100

(e.g., set the therapy delivery schedule and titrate the stimulus to optimize efficacy during sleep).

Immediately after the titration visit, the patient may return home and begin use. A therapy delivery session may begin according to the pre-defined therapy delivery schedule, which may be set to coincide with when the patient normally goes to sleep. At the beginning of a therapy delivery session, stimulus may be delayed for a period of time to allow the patient to fall asleep. The therapy delivery session may end according to the pre-defined therapy delivery schedule, which may be set to coincide with when the patient normally wakes up. The therapy delivery session may be programmed to not exceed eight hours. The patient can use the therapy controller 2500 to adjust limited aspects of therapy delivery. For example, the patient can use the therapy controller 2500 to stop, pause and restart a scheduled therapy session. In addition, the therapy controller 2500 can be used to manually control therapy delivery rather than operate according to a preset schedule. This may be beneficial when the patient has an irregular sleep schedule, for example. In this mode, the therapy controller 2500 can be used by the patient to manually start, stop, and pause a therapy session.

Surgical Implant Procedure

With continued reference to FIG. 11A, the internal components 1000 may be implanted using the following surgical procedure, which is given by way of example, not limitation. Unless specifically stated, the order of the steps may be altered as deemed appropriate. Although the INS 1100 may be surgically implanted on the right or left side, the right side is preferred to leave the left side available for implantation of cardiac devices that are traditionally implanted on the left side. The right side is also preferred for the RSL 1200 (if one RSL is used) to provide a clean respiratory signal that is less susceptible to cardiac artifact than the left side.

Figure 11B:
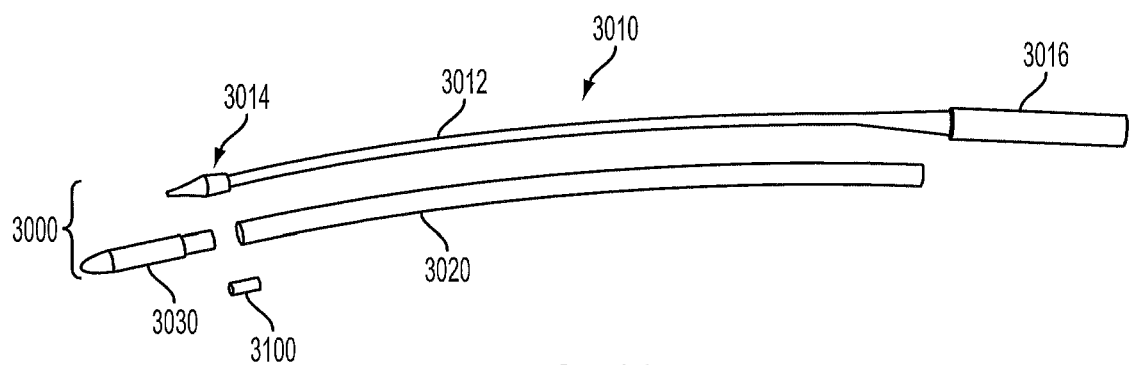
FIG. 11B is a perspective view of a disassembled tunneling tool for use in tunneling the leads of the system shown in FIG. 1.
Figure 11C:
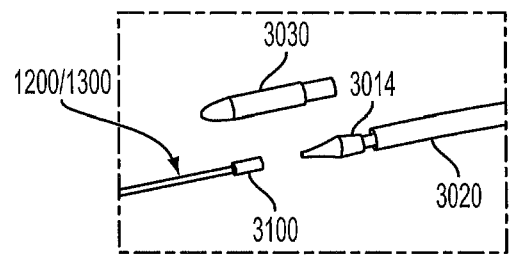
FIG. 11C is a detailed perspective view of the assembled tunneling tool shown in FIG. 11B, but with the cap removed to expose the jaws for grasping the lead carrier disposed on the proximal end of a lead.

Standard surgical instruments may be used for incisions, dissections, and formation of subcutaneous pockets. Commercially available nerve dissection instruments may be preferred for dissecting the hypoglossal nerve and placing the STL cuff 1350 on the nerve. A tunneling tool 3000, as schematically shown in FIGS. 11B and 11C, may be used for tunneling the STL 1300 and RSL 1200 leads. The tunneling tool (also referred to as tunneler) 3000 includes a relatively rigid grasper 3010, a tubular sheath 3020, and a cap 3030. The sheath 3020 and cap 3030 are sized to be slid over the grasper 3010. The cap 3030 may include a radiopaque agent such as barium sulfate loaded at 18% by weight, for example. The grasper 3010 may be formed of stainless steel and includes a shaft 3012, distal jaws (similar to an alligator clip) 3014, and a proximal handle 3016. The jaws 3014 are biased to the closed position and may be used to grasp the proximal end of the RSL 1200 or STL 1300 using the lead carrier 3100 as protection. The lead carrier 3100 may comprise a small polymeric tube with an inside diameter sized to form an interference fit with the proximal end of the RSL 1200 or STL 1330. The sheath 3020 may comprise a polymeric tube with two open ends, and the cap 3030 may comprise a polymeric tube with one open end and one closed end for blunt dissection. The proximal end of the cap 3030 may include a tapered section to fit into the distal end of the sheath 3020 and form an interference fit therewith. In the embodiment shown in FIGS. 11B and 11C, the sheath 3020 may have an outside diameter of approximately 0.37 inches and a length of about 10.9 inches. The cap may an outside diameter tapering from approximately 0.37 inches and a length of about 1.7 inches. The shaft 3012 may have a diameter of about 0.19 inches and together with the jaws 3014 may have a length sufficient to fill the length of the sheath 3020 and cap 3030. The handle 3016 may have a diameter of about 0.5 inches and a length of about 3.0 inches.

Figure 11D:
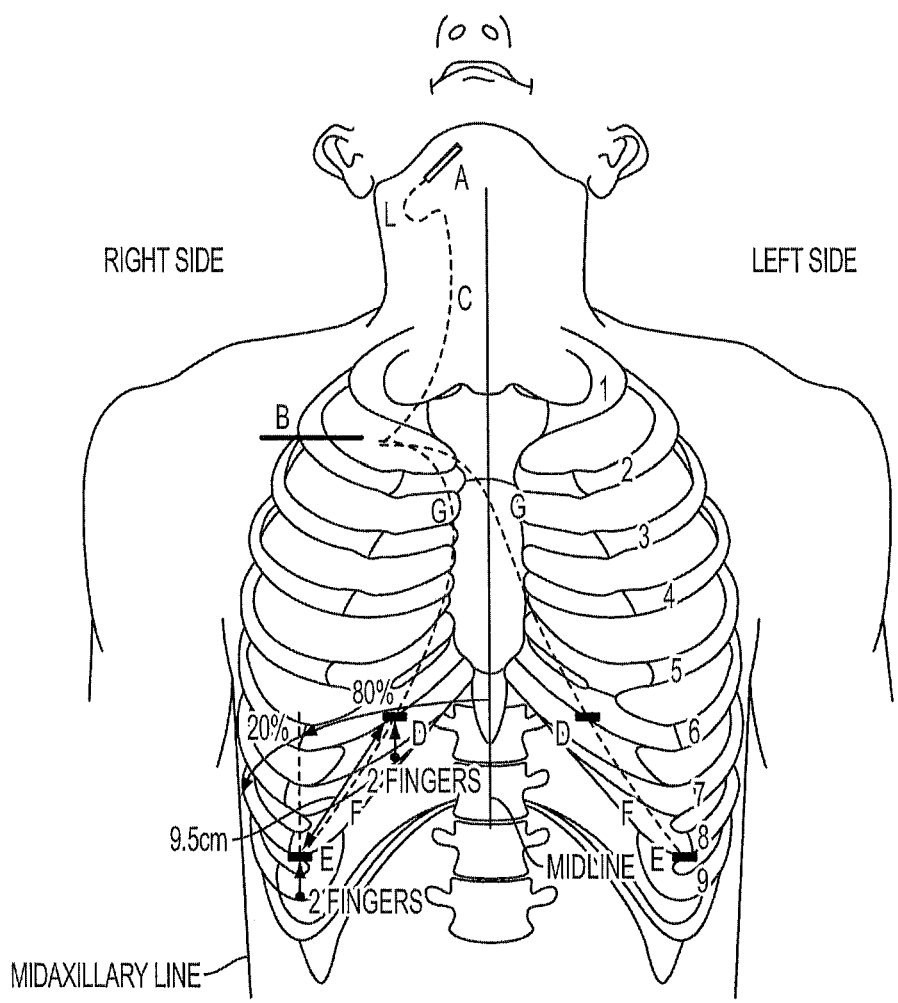
Figure 11E:
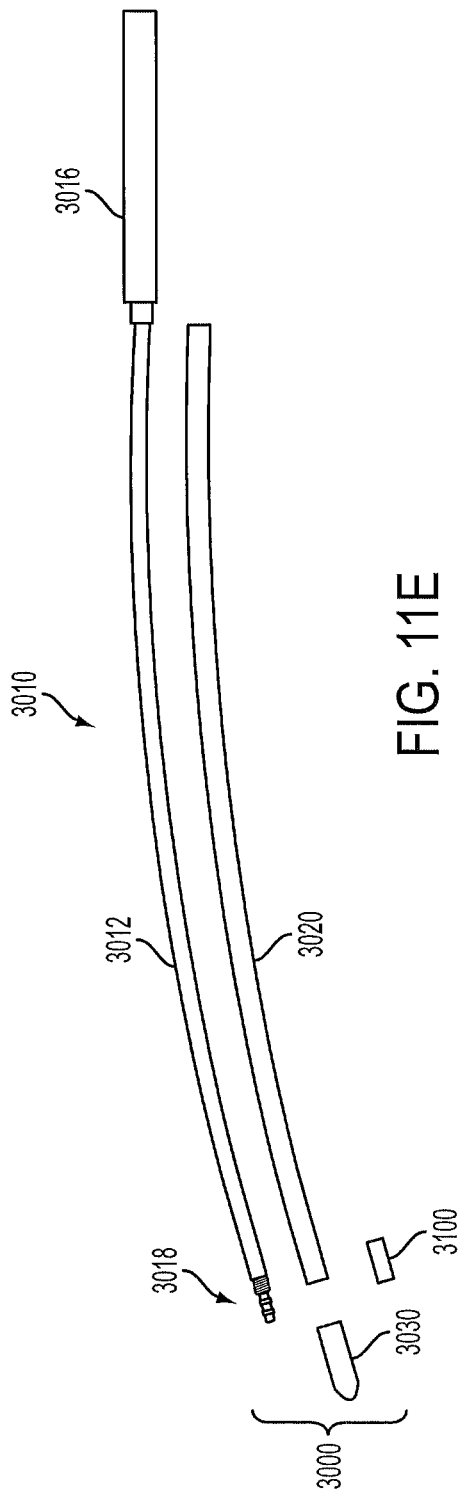
FIGS. 11E and 11F illustrate an alternative tunneling tool for use in tunneling the leads of the system shown in FIG. 1.
Figure 11F:
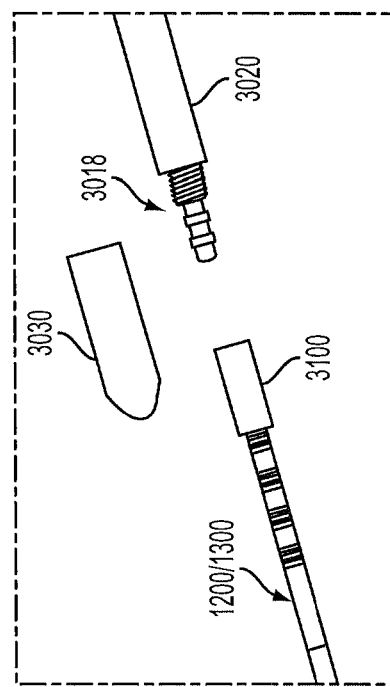

An alternative tunneling tool 3000 is schematically shown in FIGS. 11E and 11F may be used for tunneling the STL 1300 and RSL 1200. In this embodiment, the tunneling tool 3000 includes a relatively rigid grasper 3010, a tubular sheath 3020, and a cap 3030. The sheath 3020 and cap 3030 are sized to be slid over the grasper 3010. The cap 3030 may include a radiopaque agent such as barium sulfate loaded at 18% by weight, for example. The grasper 3010 may be formed of stainless steel and includes a shaft 3012, distal connector 3018, and a proximal handle 3016. The connector 3018 includes threads that mate with corresponding threads in the cap 3030. The connector 3018 may also include ring barbs that form an interference fit with the inside of the lead carrier 3100 for releasable connection thereto. The lead carrier 3100 may comprise a small polymeric tube with an inside diameter sized to form an interference fit with the proximal end of the RSL 1200 or STL 1330. The sheath 3020 may comprise a polymeric tube with two open ends, and the cap 3030 may comprise a polymeric tube with one open end and one closed end for blunt dissection. The proximal end of the cap 3030 includes internal threads to screw onto the connector 3018 and hold the sheath 3020 on the shaft 3012. In the embodiment shown in FIGS. 11E and 11F, the sheath 3020 may have an outside diameter of approximately 0.28 inches and a length of about 12.3 inches. The cap may an outside diameter tapering from approximately 0.13 inches and a length of about 1.0 inches. The shaft 3012 may have a diameter of about 0.22 inches and may have a length sufficient to fill the length of the sheath 3020. The handle 3016 may have a diameter of about 0.5 inches and a length of about 3.74 inches.

The patient is prepared for surgery using conventional practice including standard pre-operative care procedures, administration of antibiotics as appropriate, and administration of steroids as appropriate to reduce swelling around the nerve dissection. Because tongue movement must be observed during test stimulation, it is recommended that no long-acting muscle relaxants be used during surgical preparation no muscle relaxants be used during implant. General anesthesia is administered according to conventional practice and the patient is intubated using an endotracheal tube, taking care to position the endotracheal tube so that the tongue is free to protrude during test stimulation.

The neck is then extended to expose right submandibular region and a sterile field is created around the neck and thorax, taking care to avoid obstructing visualization of the oral cavity (a clear sterile drape over the mouth may be used). By way of a neck incision (A), the hypoglossal nerve is then exposed deep to the submandibular gland. Because the INS 1100 is preferably implanted on the right side to minimize cardiac artifact during respiratory sensing, this dissection is also preferably performed on the right side. The branch of the hypoglossal nerve believed to innervate the genioglossus muscle is then identified and isolated. Confirmation of correct nerve location may be achieved by performing a test stimulation later in the procedure. The identified nerve branch is then circumferentially dissected to accommodate the cuff 1350. The short side 1352 of the cuff 1350 is designed to reside on the deep side of the nerve, and the long side 1354 of the cuff 1350 is designed to reside on the superficial side of the nerve.

The appropriate sized cuff 1350 is then selected based on the nerve diameter at the intended location for cuff placement. Nerve size may be assessed using reference size (e.g., forceps of know width), a caliper, or a flexible gauge that wraps around the nerve, for example. The cuff 1350 is then opened and placed around the nerve. The strap 1356 on the cuff 1350 may be used to facilitate placement of the cuff 1350 around the nerve. A curved forceps may be placed under the nerve to grasp the strap 1356 and gently pull the cuff 1350 onto the nerve. The strap 1356 is then placed through the loop (buckle) 1358 on the cuff 1350. The cuff 1350 may be available in two sizes (small and large), and the small cuff may have an indicator mark (not shown) on the strap 1356 that should be visible after insertion through the loop 1358. If the indicator mark is not visible, the small cuff may be too small and should be replaced with a large cuff. The surgeon then verifies that the cuff 1350 is not pulling or twisting the nerve, and that there is contact between the inside of the cuff 1350 and the nerve.

A test stimulation is then performed to confirm correct positioning of the cuff 1350 on the nerve. To conduct a test stimulation, the proximal end of STL 1300 is plugged into the INS 1100 and the programmer system 2100 is used to initiate a test stimulation signal delivered from the INS 1100 to the nerve via the STL 1300. The test stimulation is performed while observing, for example, tongue movement by direct visual observation, airway caliber by nasal endoscopy, lateral fluoroscopy/cephalogram, etc. Correct placement of the cuff on the nerve may be confirmed by, for example, observing tongue protrusion, an increase in retro-glossal airway caliber, an increase in retro-palatal airway caliber, an increase in stiffness of the anterior and/or lateral walls of the retro-glossal airway with or without an increase in airway caliber, anterior movement with or without inferior movement of the hyoid bone, among others. Incorrect placement of the cuff on the nerve is indicated, for example, when the tongue is observed to retract (posterior movement), a decrease in retro-glossal airway caliber, a decrease in retro-palatal airway caliber, superior movement and particularly unilateral superior movement of the hyoid bone, among others. If necessary, the cuff 1350 may be repositioned at a different location along the length of the nerve to obtain the desired effect. The capture threshold and impedance values are recorded and the STL 1300 is disconnected from the INS 1100. A fascial wrap is then sutured over the cuff on the superficial side of the nerve.

A strain relief loop (L) in the STL 1300 is then created by arranging approximately 6 cm of the STL sigmoid body 1370 in a C-shape inside a small subcutaneous pocket formed via the neck incision (A) by blunt dissection superficially along the lateral surface of the digastric muscle in a posterior direction.

A pocket for the INS 1100 is then created by making an incision (B) down to the pectoralis fascia up to 2 finger breadths below the right clavicle. The INS 1100 is preferably implanted on the right side to minimize cardiac artifact during respiratory sensing. Blunt dissection inferior to the incision is used to create a pocket large enough to hold the INS 1100. The pocket should be inferior to the incision (B) such that the incision (B) does not reside over the INS 1100 when later placed in the pocket.

A tunnel is formed for the STL 1300 using the tunneler 3000 (sheath 3020 and cap 3030 placed over grasper 3010) to tunnel along a path (C) from the infraclavicular INS pocket to the neck incision (A). As shown in FIG. 11C, the lead carrier 3100 is then placed on the most proximal electrical contact of the STL proximal connector 1310. The cap 3030 is removed from the sheath 3020 to expose the jaws 3014 of the grasper 3010 and grab the lead carrier 3100. While holding the sheath 3020 in place, the grasper 3010 is pulled proximally to pull back the STL 1300 through the sheath 3020, taking care not to pull out the C-shaped strain relief or disturb the cuff. If the C-shaped strain relief loop (L) is pulled out, it should be replaced into the small pocket. The grasper 3010 is released from the lead carrier 3100 and the lead carrier 3100 is removed from the STL 1300. The sheath 3020 is then removed from the body leaving the STL 1300 in place. The neck incision (A) need not be closed at this time, but rather may b e closed later in the procedure allowing confirmation that the C-shaped strain relief remains in the small pocket.

The right RSL 1200 is placed near the right costal margin by making two small incisions (D and E) as shown. The medial incision (D) may be made approximately 40% (+/− 5%) of the distance from the midline to the midaxillary line, and approximately two finger breadths superior to the costal margin. The lateral incision (E) may be made approximately halfway between the medial incision (D) and the midaxillary line (i.e., extending from the medial incision (D), approximately 30% (+/−5%) of the distance from the midline to the midaxillary line), and approximately up to two finger breadths superior to the costal margin. Using the tunneler 3000 (sheath 3020 and cap 3030 placed over grasper 3010), a tunnel (F) is formed from the medial incision (D) to the posterolateral incision (E). The lead carrier 3100 is then placed on the most proximal electrical contact of the RSL 1200 proximal connector 1210. The cap 3100 is then removed from the sheath 3020 to expose the jaws 3014 of the grasper 3010 and grab the lead carrier 3100. While holding the sheath 3020 in place, the grasper 3010 is pulled proximally to pull back the RSL 1200 through the sheath 3020. The grasper 3010 is released from the lead carrier 3100 and the lead carrier 3100 is removed from the RSL 1200. The sheath 3020 is then removed from the body leaving the RSL 1200 in place. Each suture tab 1270 is secured to the underlying tissue by dissecting down to the muscle fascia adjacent the anchor tabs 1270 on the RSL 1200 and suturing each anchor tab 1270 to the muscle fascia. Permanent sutures are recommended to avoid movement of the RSL 1200 before tissue encapsulation, and braided suture material is recommended for knot retention. The left RSL 1200 is then implanted along the left costal margin in the same manner as described above.

The right RSL 1200 is then tunneled to the pocket (B) for the INS 1100. Using the tunneler 3000 (sheath 3020 and cap 3030 placed over grasper 3010), a tunnel (G) is formed from the infraclavicular pocket to the medial incision (D). The lead carrier 3100 is placed on the most proximal electrical contact of the RSL 1200 proximal connector 1210. The cap 3030 is then removed from the sheath 3020 to expose the jaws 3014 of the grasper 3010 and grab the lead carrier 3100. While holding the sheath 3020 in place, the grasper 3010 is pulled proximally to pull back the RSL 1200 through the sheath 3020. The grasper 3010 is released from the lead carrier 3100 and the lead carrier 3100 is removed from the RSL 1200. The sheath 3020 is then removed from the body leaving the RSL 1200 in place. The left RSL 1200 is then tunneled to the pocket for the INS 1100 in the same manner as described above.

The STL 1300 and RSLs 1200 are then connected to the INS 1100. Since one STL port is not used in this example, a port plug (small silicone cylinder) is inserted into header port STL-2. The RSLs 1200 are plugged into ports RSL-A and RSL-B, the STL 1200 is plugged into port STL-1 and the set screws are tightened to 1 click using a torque wrench.

A closed loop test may be performed to confirm proper operation by observation of tongue protrusion in concert with inspiration. The INS 1100 and proximal portions of the leads 1200/1300 are then placed into the infraclavicular pocket, looping the excess lead length beneath or around the INS 1100. Care should be taken not to pull out the C-shaped strain relief loop (L) in the STL sigmoid lead body 1370 while manipulating the INS 1100 into place. The INS 1100 is then sutured to underlying fascia through both suture holes found in the header 1110 of the INS 1100. Permanent sutures are recommended for to avoid movement of the INS before tissue encapsulation, and braided suture material is recommended for knot retention. Another system test may be performed at this point. After confirming that the C-shaped strain relief loop (L) is present in small pocket at neck incision, the incisions may be irrigated (optionally with an antibiotic solution) and closed using conventional techniques. After a healing period of approximately one month, the patient may undergo a sleep study to confirm proper operation of the system and to titrate therapy.

An alternative lead routing schematic is shown in FIG. 11D. In this alternative embodiment, the left and right lateral incision sites E are located 80% of the distance from the midline to the mid-axillary line, up to two finger breadths above the rib costal margin. The medial incision sites D are then located a straight line distance of 9.5 cm medial, up to two finger breadths above the rib costal margin.

Screening Methods

Figure 12:
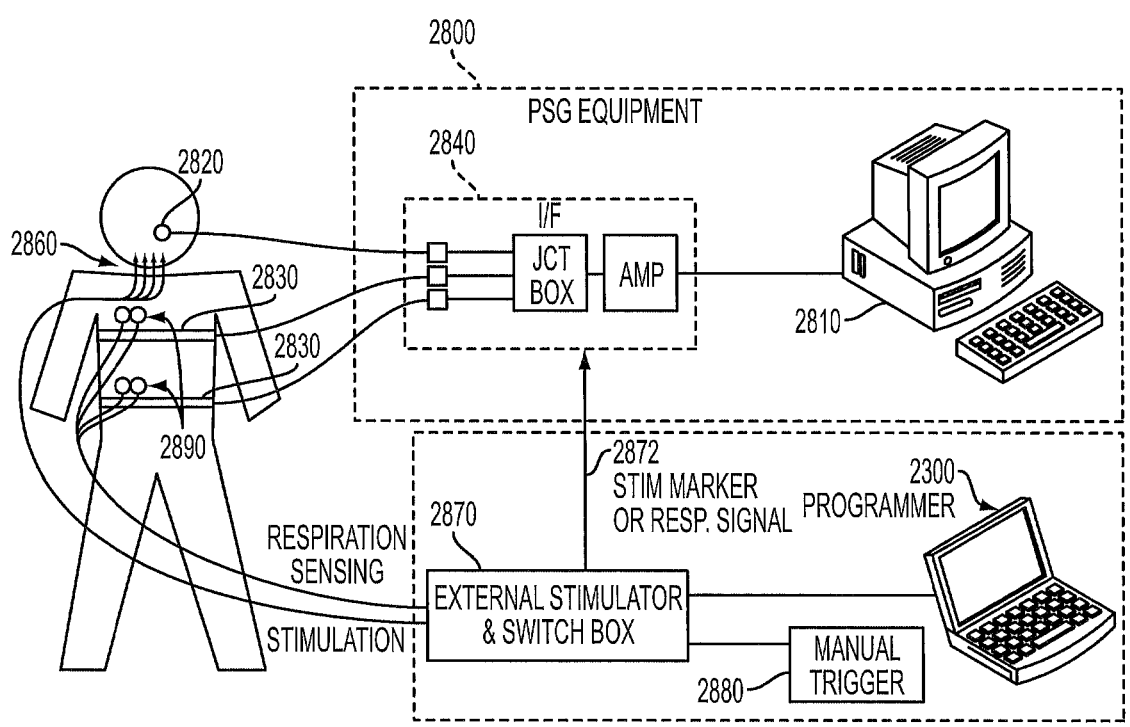
FIG. 12 is a schematic illustration of an external stimulator system and polysomnographic equipment as may be used for direct muscle stimulation using fine wire electrodes as a therapy efficacy screening method, for example.

As schematically shown in FIG. 12, an external system may be used to conduct a stimulation screening session prior to full implantation wherein the genioglossus muscle (innervated by the hypoglossal nerve) is stimulated with fine wire electrodes (FWEs) 2860 inserted submentally with a needle during an otherwise conventional sleep (PSG) study utilizing PSG equipment 2800. The FWEs 2860 may be inserted into the genioglossus under the guidance of ultrasound. Stimulation signals may be delivered to the genioglossus muscle by connecting the FWE's 2860 to an external stimulator and switch box 2870. The external stimulator and switch box 2870 may comprise the INS 1100, programmer head 2200 and programmer interface 2400 in a common housing, with the stimulation output of the INS 1100 connected to the FWEs 2860 and the sensing input of the INS 1100 connected to skin surface electrodes 2890 for bio-impedance respiration measurement. A stimulation marker output signal 2872 from the external stimulator and switch box 2870 to the PSG equipment 2800 allows stimulation and/or respiration data to be synchronized and merged with PSG data in near real time. The external stimulator and switch box 2870 may include a manually operated switch array to select a single FWE or a combination of FWEs 2860 to deliver a stimulation signal to the genioglossus muscle. With this arrangement, stimulation may be delivered via FWEs 2860 automatically triggered by inspiration measured via skin surface electrodes 2890 or manually triggered via activating a manual trigger switch 2880. The efficacy of delivering stimulus to the genioglossus muscle may be observed and measured using conventional PSG parameters. Efficacious results may be indicated by a significant reduction in apnea hypopnea index, an increase in flow, a decrease in critical closing pressure, and/or an increase in airway caliber, for example. Patients that respond adequately to stimulation during the trialing period ("responder") may receive the implanted device. Perhaps more importantly, patients that do not adequately respond to stimulation during the trialing period ("non-responder") would not receive the implanted device.

Figure 13:
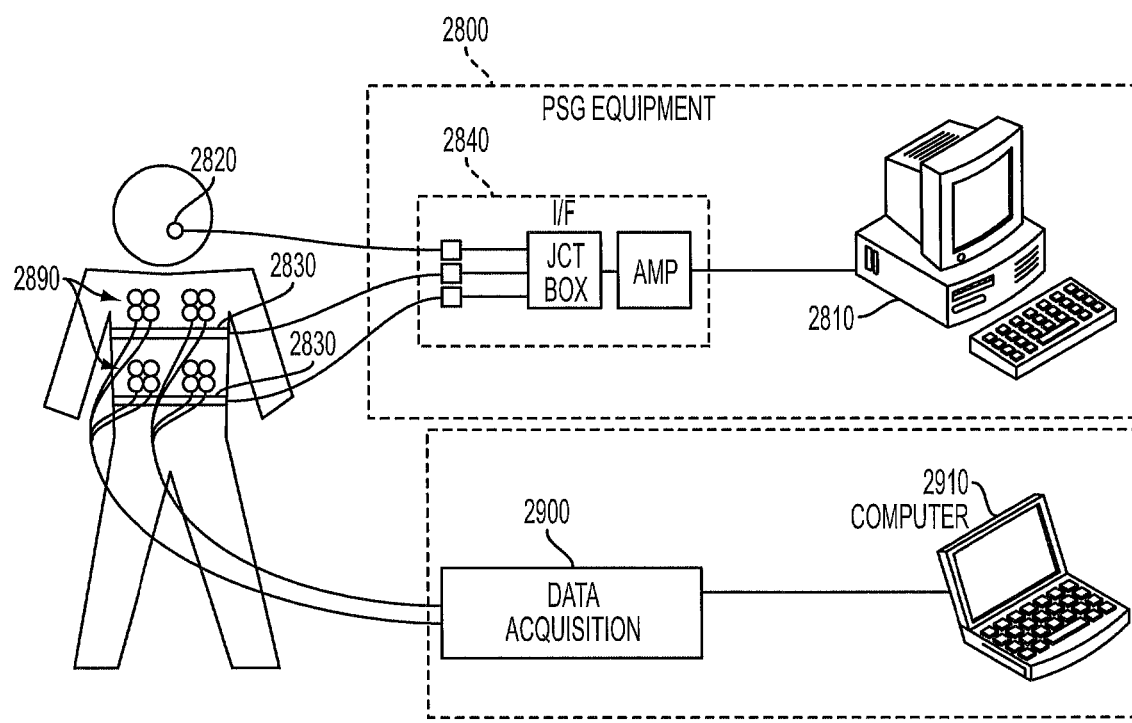
FIG. 13 is a schematic illustration of a bio-impedance monitoring system using surface electrodes and polysomnographic equipment as may be used as a respiratory sensing screening method, for example.

As schematically shown in FIG. 13, an external system may be used to conduct a respiration screening session prior to full implantation wherein skin surface electrodes are placed on the skin at or near the locations that the respiration sensing electrodes and INS would be implanted. Bio-impedance measurements may be taken during a sleep study to determine if an adequate bio-impedance signal may be obtained. In addition, different locations for the skin surface electrodes may be tested to determine the optimal locations for the respiration sensing electrodes during implantation.

The stimulation trialing period and the respiration trialing period may be combined into a single study, wherein skin surface bio-impedance measurements may be used to provide closed-loop feedback for stimulating synchronous with inspiration. Patients would then be categorized as responders or non-responders depending on the outcome of the closed-loop study.

Titrating Methods

As described previously, after implantation and a healing period of approximately one month, the patient may undergo a sleep (PSG) study to confirm proper operation of the system and to titrate therapy. Titration may utilize the set-up illustrated in FIG. 10, wherein the programmer system 2100 interfaces with the PSG equipment 2800. Titration generally involves (1) selecting an optimal respiratory sensing signal and (2) selecting optimal stimulation signal parameters (e.g., stimulation intensity, respiratory phase adjustment). After titration, therapy efficacy may be measured using standard PSG techniques. For example: a respiratory sensing vector may be selected based on signal strength and stability, reliability; the stimulation amplitude may be selected based on maximum airflow; the phase adjustment may be selected based on stimulation alignment with inspiratory airflow; and therapy efficacy may be evaluated based on elimination of indicia of sleep disordered breathing such as AHI.

Selecting an optimal respiratory sensing signal involves selecting the best vector defined by two sets of electrodes on the RSL or one set of electrodes on the RSL and the housing of the INS. Selection may be based on maximum signal strength, consistent correlation to inspiration, and maximum signal stability/reliability across sleep stages, body positions, and disordered breathing events, for example. A stable signal has a minimum probability of signal inversion. A reliable signal has a minimum probability of signal loss, and therefore may preferably have a minimum threshold of 0.2 to 0.5 Ohms peak-to-peak, for example. The optimal vector may be selected by incrementally scrolling through all or a preferred subset of possible vectors while sampling the respiration signal and comparing the signal against themselves or predefined thresholds. This scrolling technique may be performed manually (with inputs via the programmer system) or automatically (i.e., programmed). The sampling technique may also be performed manually (visual observation using programmer system) or automatically (i.e., programmed). For practical purposes, the respiration sensing vector may be evaluated while the patient is awake by having the patient assume different body positions while at resting respiration. Alternatively, the respiration sensing vector may be evaluated while the patient is asleep during different stages of sleep and during different sleep disordered breathing events. The INS is capable of streaming out data from two or more sensing vectors which allows simultaneous comparison. This may be especially useful during titration (body position testing and during sleep study) to minimize chance that evaluation of a given vector is biased by events unrelated to a given vector.

Selecting optimal stimulation signal parameters (e.g., pulse amplitude, pulse frequency, pulse width, duty cycle, phase adjust, etc.) to optimize efficacy (e.g., as measured by apnea index, hypopnea index, respiratory disturbance index, apnea-hypopnea index, and other obstructive sleep apnea efficacy measures) is preferably performed while the patient is sleeping.

The adjustable stimulation parameters include pulse frequency (range of 20 to 50 Hz, nominal 40 Hz), pulse width (range of 30 to 215 µs, nominal 90 µs), pulse amplitude (range of 0.4 to 5.0 mA, nominal 0.4 mA), duty cycle (range of 41% to 69%, nominal 50%), and phase adjust (range of −1.5 to +0.5 s, nominal −0.5 s). In general, during the stimulation titration process, it is preferable to begin with the lowest settings for pulse width (30 µs) and amplitude (0.4 mA) at a nominal frequency (40 Hz). If stimulation produces pulsatile (vibrating) contractions, the frequency may be increased to 50 Hz. The pulse width is incrementally increased to 60 µs, then to nominal (90 µs), keeping Amplitude at 0.4 mA. With the pulse width set to 90 µs, amplitude may be iterated according to the process described hereinafter. If maximum amplitude is reached and additional intensity is required, the pulse width may be increased while reducing amplitude to minimum (0.4 mA). If maximum pulse width (215 µs) is reached and additional intensity is required, frequency may be increased while reducing the pulse width to 90 µs and the amplitude to minimum (0.4 mA).

An initial step in titrating may involve defining a stimulation operating window, preferably while the patient is awake, defined at its lower limit by a capture threshold and at its upper limit by a comfort threshold. The capture threshold may be defined as the stimulation level at which some indication of a potentially beneficial effect (e.g., gross tongue movement or stiffening) is observed. The comfort threshold may be defined as the stimulation level at which the patient experiences an unacceptable sensation (e.g., pain) while awake or at which the patient partially or completely arouses (e.g., lighter stage of sleep or awake) during sleep. Human subjects have been observed to tolerate (i.e., not arouse) higher stimulation intensities while asleep than they could tolerate while awake. The operating window may be determined at the beginning of the titration sleep study (e.g. during set-up when the patient is awake) to help determine a lower limit or starting point for stimulation (capture threshold) and an upper limit or ending point for stimulation (comfort threshold), between which the stimulation level may be adjusted (e.g., increased) until an efficacious level is found.

Using the programmer system 2100 to set the stimulation parameters, the stimulation level may be initially set at the lower limit or a percentage (e.g., 50%) of the upper limit, followed by a monitoring period where efficacy is measured using standard. PSG techniques. After the initial monitoring period, the stimulation level may be incrementally increased, followed by another monitoring period. This may continue in a step-wise fashion up to the upper limit for stimulation or until no significant difference in measured efficacy is discernable between stimulation levels. If no significant difference in measured efficacy is discernable between a lower and higher stimulation level, the lower level may be selected as the desired stimulation dose.

Because efficacy measures (e.g., apnea-hypopnea index) typically take hours to collect, it may be desirable to create a controlled, flow-limited condition and measure a surrogate parameter (e.g., airflow, critical closing pressure, etc.) in order to complete the step-wise titration process in a reasonable amount of time (e.g., a single or half night sleep study). In addition, because a number of sleep conditions (e.g., sleep stage) change over the course of an all night study, it is beneficial to titrate therapy over a shorter period of time during which sleep conditions are less likely to change as significantly. To create a flow-limited state, the patient may be fitted with a CPAP (continuous positive airway pressure) device comprising a blower connected via a hose to a mask (incorporating a airflow meter such as a pneumotachometer) placed over the patient's nose and/or mouth. The CPAP device may have the capability to deliver variable pressure down to approximately 0 cm $H_2O$ or lower, in increments of 0.10 cm $H_2O$ or less, for example. Such a CPAP device is also called a P device for its ability to assist in making critical closing pressure measurements of the upper airway using techniques developed by Schwartz et al. The airway in people with obstructive sleep apnea will partially or completely occlude during sleep in the absence of adequate positive airway pressure. Thus, adjusting the CPAP pressure below the therapeutic level for a given patient will create a controlled flow-limited condition. Using these techniques, the stimulation intensity level (e.g., current, mA) or other stimulation parameter (e.g., pulse frequency, pulse duration, phase adjustment, etc.) may be titrated by progressively creating greater flow restriction while determining if a change (e.g., an increase) in a stimulation parameter (e.g., intensity) results in an increase in flow.

Figure 14A:
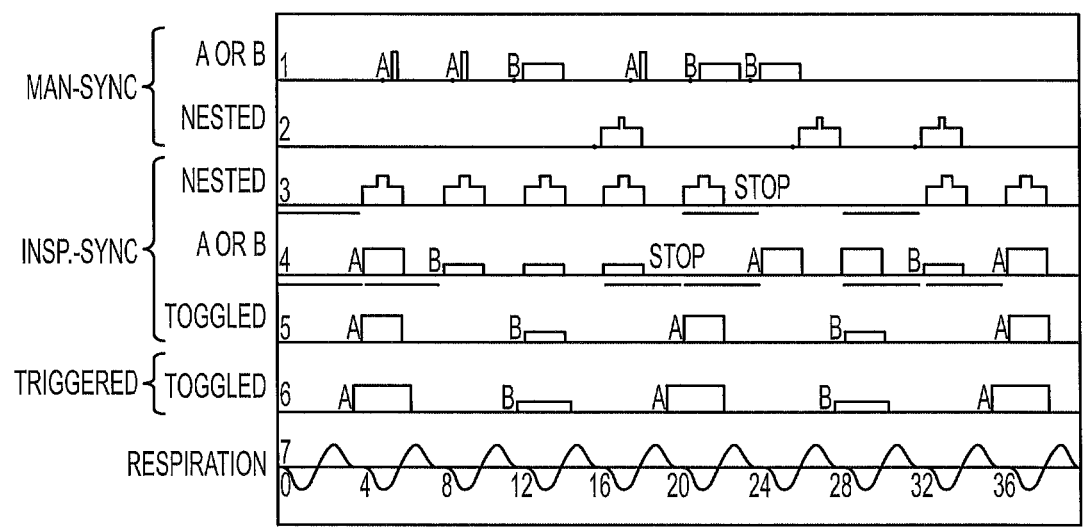
FIGS. 14A and 14B are charts showing various stimulation output modes of the implantable neurostimulator shown in FIG. 1 as may be used for therapy titration, for example.
Figure 14B:
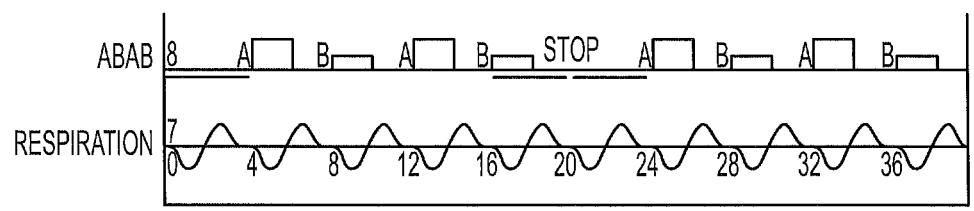

With reference to FIGS. 14A and 14B, stimulation may be delivered at different levels, different sequences, and different modes during titration. These stimulation alternatives may also be used for therapy delivery, if desired. In FIG. 14, each burst of stimulation is shown as a positive square wave and corresponds to a train of pulses as described previously. The bottom trace #7 in FIGS. 14A and 14B correspond to a respiratory flow signal wherein the negative portion of the trace corresponds to inspiration, and the positive portion of the trace corresponds to expiration.

As shown in FIGS. 14A and 14B, stimulation bursts may be delivered at different levels and in different sequences. For example, the stimulation burst may be programmed to be "A or B" (traces #1, #4 and #8), where stimulation is delivered at level "A" until commanded to deliver at level "B", or delivered at level "B" until commanded to deliver at level "A". Stimulation level "A" may correspond to a first selected level and stimulation level "B" may correspond to a second selected level, wherein the first level "A" is different than the second level "B" in terms of amplitude, pulse width and/or duration. Alternatively, the stimulation burst may be programmed to be "nested" (traces #2 and #3), where the stimulation burst comprises a composite of levels "A" and "B". As a further alternative, the stimulation burst may be programmed to "toggle" (traces #5 and #6) between the same or different level in a repeating pattern (e.g., "AB", "ABAB", "0A0B", "AA", etc.).

Also as shown in FIG. 14, stimulation may be delivered in three basic modes: manual synchronized; inspiratory synchronized; and triggered. Traces #1 and #2 illustrate manually synchronized stimulation delivery, wherein stimulation is delivered by manually entering a command via the programmer system to initiate stimulation delivery of each burst (e.g., when the user observes or anticipates inspiration on PSG, the user manually enters a command to initiate stimulation delivery). Traces #3, #4, #5 and #8 illustrate inspiratory synchronized stimulation delivery, wherein stimulation is automatically delivered according to an algorithm that predicts the inspiratory phase and initiates stimulation delivery at a desired time relative to inspiration such as at or just prior to inspiratory onset. Trace #6 illustrates triggered stimulation delivery, wherein each stimulation burst is initiated and terminated by a fiducial of the respiratory signal (e.g., positive peak, negative peak, cross-over point, etc.) which may or may not correspond to a physiological event (e.g., inspiratory onset), and which may or may not incorporate a fixed delay. Thus, in triggered mode, the stimulation burst is initiated by a fiducial and terminated by the next occurrence of the same fiducial in a repeating pattern.

The manually-synchronized A or B mode (trace #1) allows the user to program stimulation parameters for two (A & B) separately deliverable stimulation bursts. On user command, a single burst of stimulation is delivered almost immediately corresponding to A's settings, likewise for B. A and B can be defined with unique amplitudes, pulse widths, and durations; but with a common frequency. The dots on trace #1 indicate the time of manual command followed by the delivery of stimulation immediately thereafter.

The manually-synchronized nested burst (trace #2) allows the user to program stimulation parameters for a nested stimulation burst. On user command, a single burst of stimulation is delivered almost immediately corresponding to the nested burst parameters. The user defines the nested burst parameter by programming stimulation parameters for a primary mode and separately for a secondary mode. The secondary mode is of shorter duration than the primary mode. The secondary mode may be centered on the primary mode as shown, or shifted to the beginning or end of the primary mode. The two modes can be defined with unique amplitudes, pulse widths, and durations; but with a common frequency. The dots on trace #2 indicate the time of command followed by the delivery of stimulation immediately thereafter.

The inspiratory-synchronous nested mode (trace #3) delivers stimulation bursts synchronous with inspiration as determined by device and therapy delivery algorithm settings and sensed respiratory signal. This mode is similar in function to manually-synchronous nested mode (trace #2) with the following three differences: first, after user command the stimulation burst does not begin immediately but instead is delivered during the next inspiration as predicted by the therapy delivery algorithm; second, the duration of the stimulation burst is not programmed but is instead determined by the therapy delivery algorithm; and third, the nested stimulation burst will continue to be delivered on every respiratory cycle until stopped. The lines below trace #3 indicate the time window during which a command will cause therapy to begin on the following inspiration.

The inspiratory-synchronous A or B mode (trace #4) also delivers stimulation bursts synchronous with inspiration as determined by device and therapy delivery algorithm settings and sensed respiratory signal. This mode is similar to the inspiratory-synchronous nested mode (trace #3) except that the stimulation bursts comprise A or B as in the manually-synchronized A or B mode (trace #1). The selected (A or B) stimulation burst will continue to be delivered on every respiratory cycle until the other burst is selected or until stopped. The lines below trace #4 indicate the time window during which a command will cause therapy to begin or change on the following inspiration.

The inspiratory-synchronous ABAB mode (trace #8) also delivers stimulation bursts synchronous with inspiration as determined by device and therapy delivery algorithm settings and sensed respiratory signal. This mode is similar to the inspiratory-synchronous nested mode (trace #4) except that the stimulation bursts alternate between A or B on each burst. The stimulation bursts will continue to be delivered on every respiratory cycle until stopped. The lines below trace #8 indicate the time window during which a command will cause therapy to begin or end on the following inspiration.

The inspiratory-synchronous toggle mode (trace #5) also delivers stimulation bursts synchronous with inspiration as determined by device and therapy delivery algorithm settings and sensed respiratory signal. This mode is similar to the inspiratory-synchronous A or B mode (trace #4) except that the stimulation bursts are toggled. As shown, the toggled stimulation burst sequence comprises 0A0B (i.e., no stimulation, stimulation level A, no stimulation, stimulation level B), which continue to be delivered on each 4-breath series of respiratory cycles until stopped.

The triggered toggle mode (trace #6) is similar in function to the inspiratory-synchronous toggle mode (trace #5) except that the stimulation burst sequence 0A0B is initiated and terminated by a recurring fiducial of the respiratory signal.

Figure 15A:
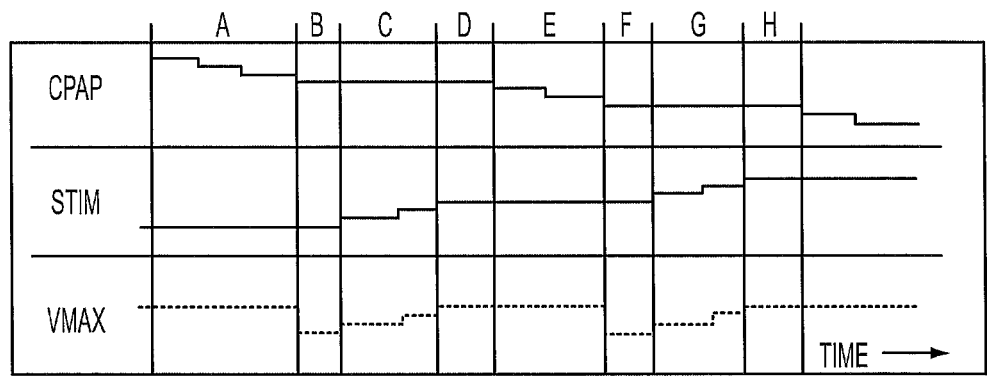

An example of a stimulation amplitude titration method is illustrated in FIG. 15A. In the illustration, three traces are shown: CPAP (pressure in cm $H_2O$); STIM (stimulation amplitude in mA); and $V_i$max (maximum inspiratory nasal airflow in mL/min as measured by pneumotach or other flow sensor). Initially, the stimulation amplitude is set to the capture threshold, and the CPAP pressure is set to an efficacious level for a given patient (typically above 5 cm $H_2O$ and determined in a prior sleep study). In period "A", the CPAP pressure is gradually decreased until a flow restricted state is reached in period "B" as detected by a drop in $V_i$max. In period "C", the stimulation amplitude is increased while the CPAP pressure remains constant until an unrestricted flow state is reached in period "D" as detected by a rise in $V_i$max. In period "E", the CPAP pressure is again gradually decreased until a flow restricted state is again reached in period "F" as detected by a drop in $V_i$max. In period "G", the stimulation amplitude is again increased while the CPAP pressure remains constant until an unrestricted flow state is reached in period "H" as detected by a rise in $V_i$max. This iterative process is repeated until the CPAP pressure reaches approximately 0 cm $H_2O$ or until no further flow benefit is observed with increasing stimulation amplitude as shown in period "I". The desired stimulation dose may be set to correspond to the lowest stimulation amplitude required to mitigate restricted flow at a CPAP pressure of approximately 0 cm $H_2O$ or the lowest stimulation amplitude for which there is no further benefit in flow, whichever is lower. In addition, therapy can be adjusted to prevent flow restrictions at a nasal pressure slightly below atmospheric to ensure efficacy under varying conditions that may otherwise compromise airflow (e.g., head flexion, nasal congestion, etc.).

Figure 15B:
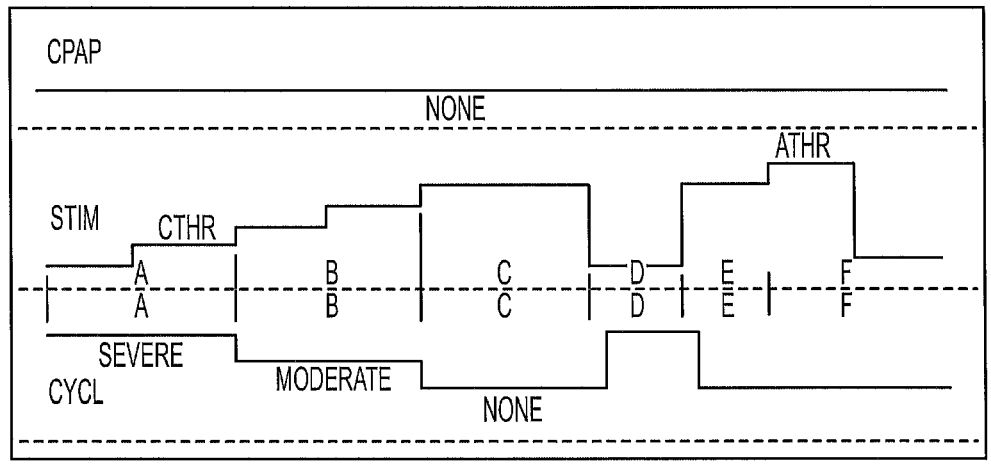

Another example of a stimulation amplitude titration method is illustrated in FIG. 15B. In addition to the stimulation amplitude titration technique described above with reference to FIG. 15A, stimulation amplitude titration can be done through a different approach that has two parts. The two parts are: with patient awake and with patient asleep. These will henceforth be known as awake titration and sleep titration respectively. During awake titration, the stimulation amplitudes that cause the lowest level of muscle contraction, tongue displacement, and muscle contraction at the threshold of comfort are recorded for the different frequency and pulse width settings.

Figure 15C:
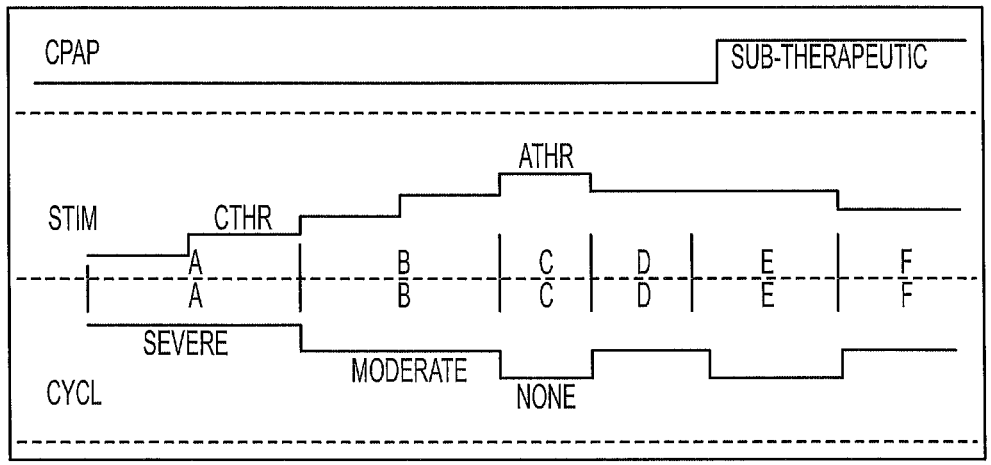

This will be followed by a sleep titration, two examples of which are illustrated in FIGS. 15B and 15C. In FIGS. 15B and 15C, three traces are shown: CPAP (pressure in cm H2O); STIM (stimulation amplitude in mA); and CYCL (cyclic breathing associated with the patient's sleep disordered breathing state). In addition, several points on the STIM trace are indicated: ATHR (the arousal threshold, or the lowest stimulation amplitude that causes arousal); CTHR (the capture threshold, or the lowest stimulation amplitude where muscle contraction is effected). Traces not shown include those of respiratory flow and oxygen saturation level; although these variables are expected to be affected by stimulation. An effect of stimulation on respiratory flow is described with reference to FIG. 15A.

In FIG. 15B, sleep titration is carried out with the patient at atmospheric pressure and preferably in the supine position. However, this stimulation level titration is expected to be repeated throughout the sleep titration period with the patient in different conditions, including different body positions and sleep stages. After onset of sleep, in region A, the patient is experiencing what to them would be considered severe sleep disordered breathing. Stimulation amplitude is also periodically increased in region A. During these periodic increases the lowest stimulation amplitude that causes muscle contraction is also identified. In region B, stimulation amplitude continues to be periodically increased, which reduces the degree of but does not abolish the sleep disordered breathing that the patient experiences. In region C after continued increase of the stimulation amplitude a level that abolishes the sleep disordered breathing of the patient is achieved. If this stimulation amplitude is reached in conditions considered to be most challenging, then this stimulation level could be considered the therapeutic level. In region D stimulation is turned OFF, which causes the patient to go into sleep disordered breathing. In region E, the therapeutic stimulation level is turned back ON and the patient's sleep disordered breathing is abolished once again. In region F, continued periodic increase of stimulation amplitude leads to levels that cause arousal. The arousal threshold is thus identified. In this titration process, the stimulation level that abolishes the patient's sleep disordered breathing without causing arousal and with the patient in the most challenging conditions is identified.

In FIG. 15C, sleep titration is started with the patient at atmospheric pressure. However, if a stimulation level that completely abolishes sleep disordered breathing without causing arousal is not achieved, then some sub-therapeutic CPAP (the patient's therapeutic CPAP will have been identified in a previous sleep study) could be used to complement stimulation for the delivery of therapy. After onset of sleep, in region A, the patient is experiencing what to them would be considered severe sleep disordered breathing. Stimulation amplitude is also periodically increased in region A. During these periodic increases the lowest stimulation amplitude that causes muscle contraction is also identified. In region B, stimulation amplitude continues to be periodically increased, which reduces the degree of but does not abolish the sleep disordered breathing that the patient experiences. In region C, continued periodic increase of stimulation amplitude leads to levels that cause arousal. The arousal threshold is thus identified. Note that, in this example, the stimulation level that causes arousal is reached before the level that completely abolishes sleep disordered breathing could be. In region D, a stimulation level that is just below the arousal threshold is maintained and the patient holds in moderate sleep disordered breathing. In region E, a subtherapeutic CPAP level that abolishes the patient's disordered breathing is applied. This identifies the level of CPAP that complements stimulation in some patients. In region F, stimulation is either turned down or OFF from the level just below the arousal threshold, leading the patient to go into disordered breathing. In some cases, where the patients' sleep disordered breathing cannot be abolished by stimulation only, some CPAP pressure may be used to complement stimulation. This could help increase the likelihood of CPAP compliance of some patients since the CPAP pressure is reduced. In addition, it could help analyze how far patients are from being completely treated by either stimulation or CPAP.

Figure 16A:
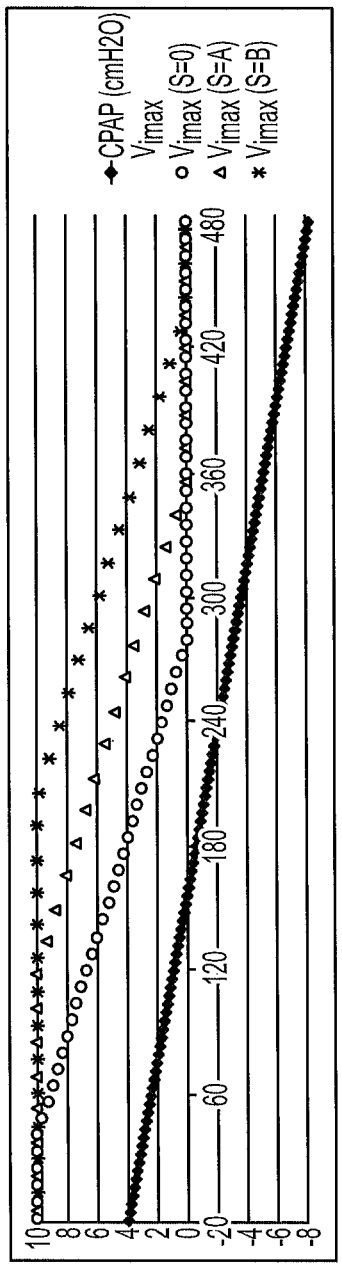
Figure 16B:
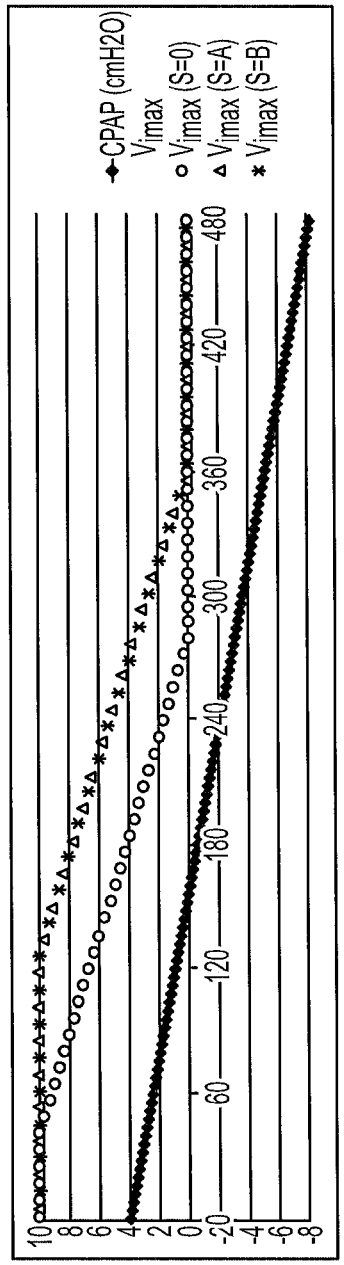

Another example of a stimulation amplitude titration method is illustrated in FIGS. 16A and 16B. This method may be carried out over a period of breaths (e.g., 4-10) or very slowly over several minutes (e.g., dozens of breaths to verify that optimal stimulation intensity has been identified). In the illustration, four traces are shown: one trace for CPAP pressure (designated by a solid diamond, pressure in cm $H_2O$); and three traces for $V_i$max (maximum inspiratory nasal airflow in mL/min as measured by pneumotach or other flow sensor) for stimulation amplitudes "0", "A" and "B". $V_i$max at stimulation amplitude "0" (designated by an open circle) corresponds to flow with stimulation off. $V_i$max at stimulation amplitude "A" (designated by an open triangle) corresponds to flow with stimulation set to a value "A", and $V_i$max at stimulation amplitude "B" (designated by an asterisk) corresponds to flow with stimulation set to a value "B", where "A" is slightly less than "B". Stimulation is delivered alternately at levels "A" and "B" with intermediate "0" levels (e.g., "0A0B"). Alternatively, stimulation may be delivered alternately at levels "A" and "B" without intermediate "0" levels (e.g., "AB"), which may be advantageous because the sequence may be executed faster and because arousal may otherwise occur due to low flow conditions at stimulation level "0".

Initially, the CPAP pressure is set to an efficacious level for a given patient (typically above 5 cm $H_2O$ and determined in a prior sleep study). With the stimulation amplitude set to "0" (i.e., stimulation is turned off), the CPAP pressure is gradually decreased while measuring $V_i$max to obtain a base-line reading when flow is un-restricted (beginning) and subsequently restricted. The stimulation amplitude is then set to alternate between "A" and "B", where "A" is set to the capture threshold and "B" is set slightly higher than "B" (e.g., 0.1-1.0 mA higher). The CPAP pressure is then gradually decreased (or dropped for a short series of breaths and returned to baseline if needed to maintain a passive state) while measuring $V_i$max to determine the flow at each stimulation level as shown in FIG. 16A. The values of "A" and "B" are incrementally increased and the CPAP pressure is again gradually decreased while measuring flow. This iterative process is repeated until the traces converge as shown in FIG. 16B, demonstrating that no further benefit in flow is realized with an increase in stimulation. The therapy setting may then be set to correspond to the lower stimulation amplitude value ("A") where the traces for "A" and "B" converge. Note that FIGS. 16A and 16B display the case where no arousal occurs during the gradual decrease in CPAP pressure. In practice, it is expected that arousals will occur before the process can be taken to complete conclusion as shown in the Figures. In the event of arousals, the iterative process is repeated based upon convergence of the traces prior to the point of arousal.

Figure 17:
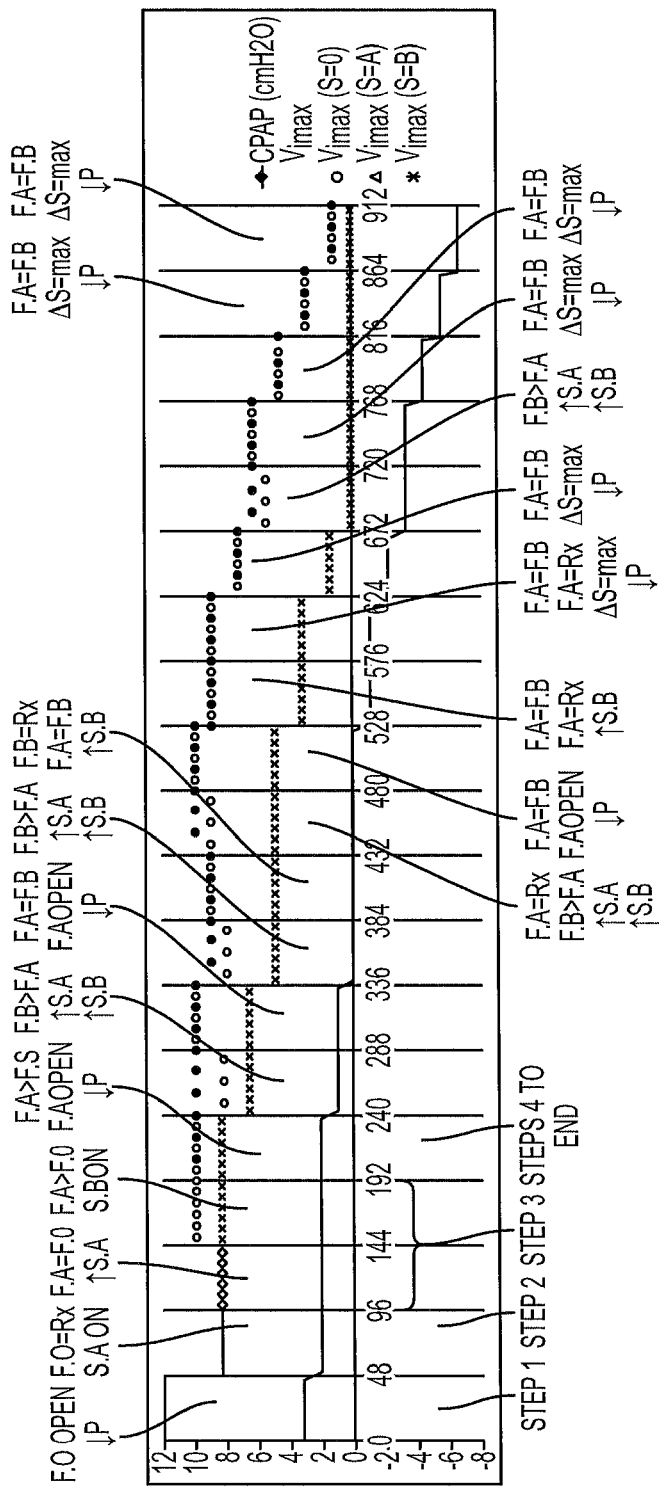

Another example of a stimulation amplitude titration method is illustrated in FIG. 17. FIG. 17 illustrates this method using a stimulation sequence comprising "0A0B", although a stimulation sequence comprising "AB" may be used as an alternative. In FIGS. 17 and 18: "F" refers to peak inspiratory flow; "F.0" refers to flow with no stimulation; "F.A" refers to flow with stimulus intensity "A"; "F.B" refers to flow with stimulus intensity "B"; "OPEN" indicates that the airway is open, with no flow limitation; "Rx" indicates that the airway is restricted (steady state flow limitation); "↑S.A" (or "↑S.B") indicates that the intensity of stimulus "A" (or "B") should be increased; "↓P" indicates that CPAP (nasal) pressure should be reduced; "ΔS" is the difference between stimuli A and B; and "ΔS=max" is when stimulus "B" is the maximum difference in intensity from stimulus "A" that will be tested (1.0 mA is recommended for this value).

Step 1 (holding pressure) in this method involves adjusting CPAP (nasal) pressure to the lowest holding pressure where maximum inspiratory flow ($V_i$,max) is not limited, and recording various data. Step 2 (attain oscillation/steady state flow limitation) involves reducing CPAP (nasal) pressure until flow oscillation occurs, recording data, increasing CPAP (nasal) pressure until oscillations cease, thereby achieving steady-state flow limitation (SSFL), and recording data. Step 3 (activation threshold, defined as lowest stimulation intensity with a measurable effect on flow) involves selecting triggered toggled stimulation mode 0A0B with stimulation amplitude level A=stimulation amplitude level B=0.4 mA, and pulse width=30 microseconds (if no effect <90 microseconds, increment to 90 microseconds). Then, with stimulation amplitude level A=B, both amplitude levels A and B are incrementally increased until flow differs between stimulated breaths (level=A=B) and non-stimulated breaths (level=0). If necessary, CPAP (nasal) pressure may be adjusted to ensure SSFL during non-stimulated breaths. Step 4 (optimize stimulation level) involves selecting triggered toggled stimulation mode 0A0B with stimulation amplitude level A=activation threshold (determined in step 3) and stimulation amplitude level B=smallest increment greater than level A, and then executing the following sub-routine:

(a) While there is a significant difference in Vi,max (>10%) between Stim A and B, increase both A and B amplitudes by same amount (0.1 mA-0.5 mA) until no significant difference in Vi,max is observed;

(b) If Stim A breaths not flow limited, reduce CPAP (nasal) pressure until flow limitation is achieved and return to step (a); else, continue to (c);

(c) If Max Delta Slim (difference between Slim A and Slim B=1.0 mA, for example) is reached, decrement CPAP (nasal) pressure; else increase Slim B; continue to (d);

(d) Stop if either the lowest CPAP pressure level to be tested is reached (e.g., atmospheric or sub-atmospheric), or if maximum stimulation intensity of the INS is reached; else return to (a).

The therapy setting may then be set to correspond to the lower stimulation amplitude value ("A" or "B") where there is no increase in flow benefit. Optionally an additional margin may be added to the setting (a fixed value or a percentage of the setting, e.g., 10% to 20%) to accommodate changing physiologic conditions.

Figure 18A:
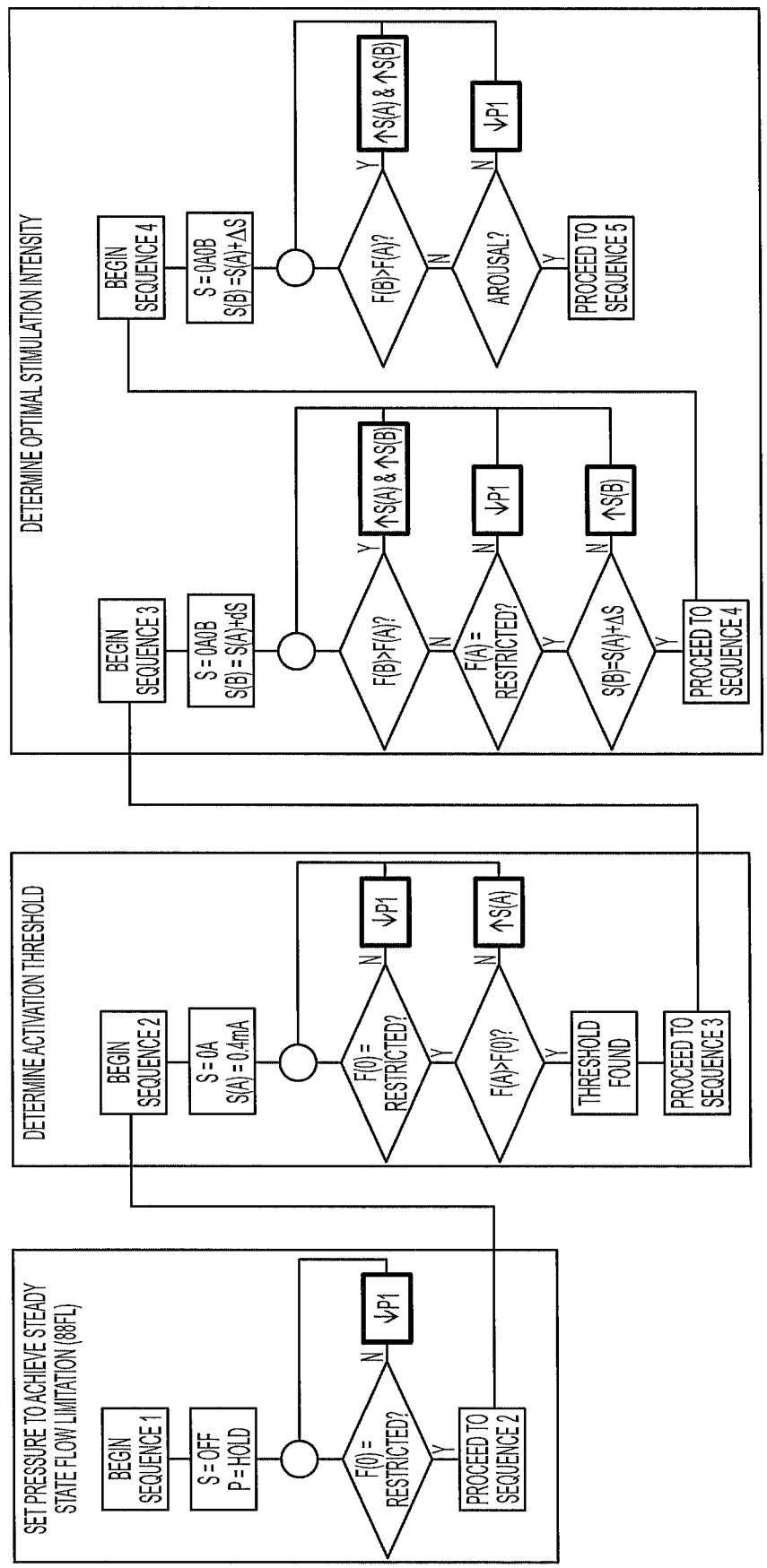

FIG. 18A is a flow chart illustrating the method described with reference to FIG. 17. FIG. 18B provides a legend for the flow chart of FIG. 18A.

From the foregoing, it will be apparent to those skilled in the art that the present invention provides, in exemplary non-limiting embodiments, devices and methods for nerve stimulation for OSA therapy. Further, those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A programmable neurostimulator comprising:
a processor configured to:
deliver a respiratory therapy to a subject;
titrate a stimulation setting of the respiratory therapy while the subject is awake by delivering a first set of stimulation pulses at a plurality of first stimulation setting values between a lower limit defined by a capture threshold corresponding to a beneficial effect of the respiratory therapy and an upper limit defined by a comfort threshold corresponding to an unacceptable sensation experienced by the subject; and
subsequently, while the subject is asleep, repeat the step of titrating the stimulation setting of the respiratory therapy by delivering a second set of stimulation pulses at a plurality of second stimulation setting values, wherein one or more of the plurality of second stimulation setting values is different than one or more of the plurality of first stimulation setting values and the plurality of second stimulation setting values are between the lower limit defined by the capture threshold and a second upper limit defined by a threshold at which the subject is expected to at least partially arouse from sleep.

2. The programmable neurostimulator of claim 1, wherein the processor is configured to repeat the step of titrating the stimulation setting of the respiratory therapy by further subsequently delivering a third set of stimulation pulses at a plurality of third stimulation setting values, wherein one or more of the plurality of third stimulation setting values is different than one or more of the plurality of second stimulation setting values.

3. The programmable neurostimulator of claim 2, wherein the processor is configured to repeat the step of titrating the stimulation setting of the respiratory therapy by further comparing responses of the subject to the second and third sets of stimulation pulses.

4. The programmable neurostimulator of claim 3, wherein the processor is configured to compare the responses of the subject by comparing air flow of the subject responsive to the second and third sets of stimulation pulses.

5. The programmable neurostimulator of claim 4, wherein the processor is further configured to deliver controlled pressure to an airway of the subject while performing at least one of titrating or repeating the step of titrating the stimulation setting of the respiratory therapy.

6. The programmable neurostimulator of claim 5, wherein the controlled pressure creates a flow-limited state.

7. The programmable neurostimulator of claim 2, wherein the processor is configured to deliver the second and third sets of stimulation pulses in a sequence to define a stimulation pattern.

8. The programmable neurostimulator of claim 7, wherein the stimulation pattern comprises at least one of a period of no stimulation, an AB pattern, an ABAB pattern, an 0A0B pattern, or an AA pattern.

9. The programmable neurostimulator of claim 7, wherein the processor is configured to deliver the stimulation pattern in at least one of a manual mode, a synchronized mode, or a triggered mode.

10. The programmable neurostimulator of claim 2, wherein the third set of stimulation pulses comprises a different amplitude than the second set of stimulation pulses.

11. The programmable neurostimulator of claim 1, wherein the processor is configured to titrate the stimulation of the respiratory therapy such that the titrating defines a stimulation level operating window having a capture stimulation level and a maximum comfort stimulation level inclusively between which the programmable neurostimulator is configured to deliver the first set of stimulation pulses; and wherein the capture stimulation level corresponds to respiratory muscle movement and the maximum comfort stimulation level is greater than the capture stimulation level.

12. The programmable neurostimulator of claim 11, wherein the respiratory muscle movement is at least one of an initial response of the respiratory muscle to a stimulation, a tongue movement, or a tongue stiffening.

13. The programmable neurostimulator of claim 11, wherein the maximum comfort stimulation level corresponds to at least one of a sensation of pain or an inability to sleep.

14. The programmable neurostimulator of claim 11, wherein the processor is configured to deliver the second set of stimulation pulses at a magnitude that is greater than the maximum comfort stimulation level.

15. The programmable neurostimulator of claim 1, wherein the processor is configured to deliver the awake titration by performing at least one of:
   determining a stimulation level operating window;
   determining a stimulation level that causes muscle contraction; or
   determining a stimulation level that causes subject discomfort.

16. A programmable neurostimulator comprising:
   a processor configured to:
      deliver a respiratory therapy to a subject;
      identify a stimulation operating window for the respiratory therapy,
         wherein the stimulation operating window includes a first threshold and a second threshold, wherein the first threshold is defined as a first level of stimulation at which a beneficial response is observed in an upper airway of the subject, and wherein the second threshold is defined as a second level of stimulation greater than the first level of stimulation;
      wherein the second threshold comprises an awake level at which the subject experiences an unacceptable sensation while awake and an asleep level greater than the awake level at which the subject is expected to at least partially arouse from sleep; and
      wherein the programmable neurostimulator is configured to identify the stimulation operating window for the respiratory therapy by:
         titrating a stimulation setting of the respiratory therapy while the subject is awake by delivering successive stimulation bursts until the first threshold and the awake level of the second threshold are identified, wherein at least one of the successive stimulation bursts includes an intensity different than another one of the successive stimulation bursts; and
         subsequently repeating the step of titrating the stimulation setting of the respiratory therapy while the subject is asleep by delivering successive stimulation bursts until the asleep level of the second threshold is identified.

17. The programmable neurostimulator of claim 16, wherein the processor is further configured to deliver controlled pressure to an upper airway of the subject while performing at least one of titrating or repeating the step of titrating the stimulation setting.

18. The programmable neurostimulator of claim 17, wherein the controlled pressure creates a flow-limited state.

19. The programmable neurostimulator of claim 16, wherein the beneficial response comprises a muscle contraction.

20. The programmable neurostimulator of claim 16, wherein the unacceptable sensation comprises at least one of pain, arousal from sleep, or inability to sleep.

* * * * *